United States Patent
Hashimoto et al.

(10) Patent No.: US 10,309,967 B2
(45) Date of Patent: Jun. 4, 2019

(54) METHODS OF DIAGNOSING BIPOLAR DISORDERS AND SCREENING FOR THERAPEUTIC COMPOUNDS

(71) Applicant: National University Corporation Chiba University, Chiba (JP)

(72) Inventors: Kenji Hashimoto, Chiba (JP); Takashi Futamura, Tokushima (JP); Noriko Yoshimi, Tokushima (JP); Takeo Yoshikawa, Wako (JP); Yoshimi Iwayama, Wako (JP); Mikael Landen, Gothenburg (SE)

(73) Assignee: National University Corporation Chiba University, Chiba (JP)

( * ) Notice: Subject to any disclaimer, the term of this patent is extended or adjusted under 35 U.S.C. 154(b) by 330 days.

(21) Appl. No.: 15/156,352

(22) Filed: May 17, 2016

(65) Prior Publication Data

US 2016/0341740 A1    Nov. 24, 2016

Related U.S. Application Data

(60) Provisional application No. 62/162,878, filed on May 18, 2015.

(51) Int. Cl.
*C12P 19/34* (2006.01)
*G01N 33/68* (2006.01)
*C12Q 1/6883* (2018.01)

(52) U.S. Cl.
CPC ....... *G01N 33/6812* (2013.01); *C12Q 1/6883* (2013.01); *C12Q 2600/136* (2013.01); *C12Q 2600/156* (2013.01); *C12Q 2600/158* (2013.01); *G01N 2500/00* (2013.01); *G01N 2570/00* (2013.01); *G01N 2800/304* (2013.01)

(58) Field of Classification Search
CPC ............ C12Q 1/6883; C12Q 2600/136; C12Q 2600/156; C12Q 2600/158; G01N 2500/00; G01N 2570/00; G01N 2800/304; G01N 33/6812
USPC ....................................................... 435/91.2
See application file for complete search history.

(56) References Cited

U.S. PATENT DOCUMENTS

| | | | |
|---|---|---|---|
| 2010/0003694 A1* | 1/2010 | Bahn .................. | C07K 14/48 435/7.1 |
| 2014/0113912 A1* | 4/2014 | Loebel ................ | A61K 31/496 514/254.04 |

OTHER PUBLICATIONS

Money et al., Metabolomics, vol. 3, No. 1, pp. 1-7, (Year: 2013).*
Albert et al., Journal of Affective Disorders, vol. 173, pp. 170-175, November (Year: 2014).*

* cited by examiner

*Primary Examiner* — Cynthia B Wilder
(74) *Attorney, Agent, or Firm* — Kilyk & Bowersox, P.L.L.C.

(57) ABSTRACT

Methods of diagnosing, confirming a diagnosis of, and determining a predisposition for a bipolar disorder in a subject are provided. An amount of at least one of biomarker from the cerebrospinal fluid and/or serum of a subject is measured, for example, isocitric acid. The amount of the at least one biomarker can be compared with a control amount of the at least one biomarker in a corresponding sample collected from a subject without the bipolar disorder. An increase or decrease in the amount of the particular biomarker or biomarkers measured can be indicative that the subject has the bipolar disorder or a predisposition for the bipolar disorder. Methods of identifying a compound for preventing and/or treating a bipolar disorder are also provided based on the expression level of an isocitric acid dehydrogenase 3 alpha and/or beta-subunit gene, and/or based on one or more metabolite biomarker.

11 Claims, 2 Drawing Sheets

METHODS OF DIAGNOSING BIPOLAR DISORDERS AND SCREENING FOR THERAPEUTIC COMPOUNDS

This application claims the benefit under 35 U.S.C. § 119(e) of prior U.S. Provisional Patent Application No. 62/162,878 filed May 18, 2015, which is incorporated in its entirety by reference herein.

BACKGROUND OF THE INVENTION

The present invention relates to methods for diagnosing a bipolar disorder and screening for therapeutic compounds for treating or preventing a bipolar disorder.

Bipolar disorder (BD) is a major psychiatric disease characterized by episodes of depression and mania or hypomania interspaced by periods of euthymia. With a typical age of onset in late adolescence or early adulthood, BD is a major health problem that involves continuous monitoring and often lifelong treatment, and places a substantial economic burden on healthcare systems and society. A recent Swedish resource use study estimated the average annual cost to 28,011 euro/year/patients, and a 2009 US-study estimated the direct and indirect costs of BD to be 151 billion dollars.

Although a number of studies of families and twins show the significance of genetic factors affecting susceptibility to BD, the precise pathogenesis of BD is not well understood. BD may be a neuroinflammatory or neurodegenerative disorder, in which relapses are toxic, indicating the utility of early detection to prevent an otherwise negative prognosis. However, accumulating evidence suggests that mitochondrial dysfunction plays a key role in the pathogenesis of BD.

Metabolomics is the profiling of small molecule metabolites and provides the potential to characterize specific metabolic phenotypes associated with a disease. Metabolomics has an advantage over other "omics" techniques in that it directly samples the metabolic changes in an organism and integrates information from changes at the gene, transcript, and protein levels, as well as posttranslational modifications. Metabolomics analysis of postmortem brain samples from BD patients and controls have been reported. Tissue concentration of small molecules, such as amino acids, in brain samples is known to be significantly affected by postmortem interval (PMI). Therefore, metabolomic analyses using postmortem brain samples might not be useful for determination of biomarkers. Cerebrospinal fluid (CSF) is a highly relevant sampling substrate for the in vivo study of brain disorders as it reflects the metabolic status and the biochemistry of the brain. Metabolomic profiles of CSF in patients and controls therefore have the potential to reveal protein differences linked to the pathogenesis of BD that might have value as biomarkers.

Capillary electrophoresis time-of-flight mass spectrometry (CE-TOFMS) is a state-of-the-art metabolome analysis technique. The advantages of CE-TOFMS analysis include extremely high resolution, versatility, and ability to simultaneously quantify virtually all the charged low-molecular-weight compounds in a sample. Two studies using this technique have shown robust changes in four molecules (arginine, taurine, 5-oxoproline, and lactic acid) in the plasma of autism spectrum disorders, and significant changes in the five molecules (creatine, betaine, nonanoic acid, benzoic acid, and perillic acid) in the plasma of first-episode, medicated patients with schizophrenia. However, there are no reports using this technique in CSF samples from BD patients.

Accordingly, there is a need for methods of diagnosing bipolar disorders and identifying compounds having potential efficacy against bipolar disorders.

NON-PATENT LITERATURE

The following references are incorporated in their entireties by reference herein:
Belmaker, N. Eng. J. Med. 2004; 351(5):476-486.
Taylor, Nat. Rev. Neurol. 2009; 5(9):484-491.
Crump et al., JAMA Psychiatry. 2013; 70(9):931-939.
Kleine-Budde et al., Bipolar Disord. 2014; 16(4):337-353.
Ekman et al., Soc. Psychiatry Psychiatr. Epidemiol. 2013; 48(10):1601-1610.
Dilsaver, J. Affect. Disord. 2011; 129(1-3):79-83.
Craddock et al., Lancet 2013; 381(9878):1654-1662.
Jakobsson et al., Neuropsychopharmacology. 2014; 39(10): 2349-2356.
Ekman et al., Acta Psychiatr. Scand. 2010; 122(6):507-515.
Iwamoto et al., Hum. Mol. Genet. 2005; 14(2):241-253.
Kato, Trends Neurosci. 2008; 31(10): 495-503.
Quiroz et al., Neuropsychopharmacology. 2008; 33(11): 2551-2565.
Konradi et al., Neurobiol. Dis. 2012; 45(1):37-47.
Andreazza et al., Int. J. Neuropsychopharmacol. 2014; 17(7):1039-1052.
de Sousa et al., Expert Opin. Ther. Targets. 2014; 18(10): 1131-1147.
Holmes et al., Cell. 2008; 134(5):714-717.
Quinones et al., Neurobiol. Dis. 2009; 35(2):165-176.
Davies et al., Proc. Natl. Acad Sci USA. 2014; 111(29): 10761-10766.
Lan et al., Mol. Psychiatry. 2009; 14(3):269-279.
Perry et al., J. Neurochem. 1981; 36(2):406-410.
Hashimoto et al., Biol. Psychiatry. 2007; 62(11):1310-1316.
Soga et al., Anal. Chem. 2009; 81(15):6165-6174.
Soga et al., J. Proteome Res. 2003; 2(5):488-494.
Kuwabara et al., PLoS One. 2013; 8(9):e73814.
Koike et al., Transl. Psychiatry. 2014; 4:e379.
Ryden et al., J. Neural. Transm. 2009; 116(2):1667-1674.
PÅlsson et al., Eur. Neuropsychopharmacol. 2015; 25(1): 133-140.
Sachs et al., Biol. Psychiatry. 2003; 53(1):1028-1042.
Sheehan et al., J. Clin. Psychiatry. 1998; 59(Suppl 20):22-33.
Saunders et al., Addiction. 1993; 88(6):791-804.
Kim et al., Schizophr. Bull. 2009; 35(6):1031-1033.
Kim et al., Neuropsychopharmacology. 2010; 35(2):473-482.
Yamada et al., Hum. Genet. 2012; 131(3):443-451.
Allen et al., Technometrics. 1974; 16(1):125-127.
Miller et al., Subset selection in regression Subset regression. Chapman and Hall. 1974.
Hunziker et al., Crit. Care Med. 2011; 39(7):1670-1674.
Wadelius et al., Blood. 2009; 113(4):784-792.
Tong et al., Biometals. 2007; 20(3-4):549-564.
McKenney et al., J. Clin. Invest. 2013; 123(9):3672-3677.
Cairns et al., Cancer Discov. 2013; 3(7):730-741.
Hartong et al., Nat. Genet. 2008; 40(10):12030-1234.
Dudley et al., J. Affect. Disord. 2015; 175C:251-255.
Konradi et al., Arch. Gen. Psychiatry. 2004; 61(3):300-308.
Sun et al., J. Psychiatry Neurosci. 2006; 31(3):189-196.
Andreazza, et al. Arch. Gen. Psychiatry. 2010; 67(4):360-368.
Kato et al., J. Affect. Disord. 1994; 31(2):125-133.
Port et al., Psychiatry Res. 2008; 162(2):113-121.
Dager et al., Arch. Gen. Psychiatry. 2004; 61(5):450-458.

Soga et al., Anal. Chem. 2000; 72(6):1236-1241.
Soga et al., Anal. Chem. 2002; 74(10):2233-2239.
Sugimoto et al., Metabolomics. 2009; 6(1):78-95.
Karanti et al., J. Affect. Disord. 2014; 174:303-309.
Sellgren et al., Acta Psychiatr. Scand. 2011; 124(6):447-453.
Rydén et al., Acta Psychiatr. Scand. 2009; 120(3):239-246.
Korn et al. Nat. Genet. 2008; 40(10):1253-1260.
International HapMap 3 Consortium, Altshuler et al., Nature. 2010; 467(7311):52-58.
Browning et al., Am. J. Hum. Genet. 2007; 81(5):1084-1097.
Purcell et al., Am. J. Hum. Genet. 2007; 81(3):559-575.
Talab et al., Eur. J. Pharmacol. 2010; 647(1-3):171-177.
Niles et al., Int. J. Neuropsychopharmacol. 2012; 15(9): 1343-1350.

SUMMARY OF THE PRESENT INVENTION

A feature of the present invention is to provide a method that enables the diagnosis of a bipolar disorder in a subject.

Another feature of the present invention is to provide a method that enables the confirmation of a bipolar disorder in a subject.

A further feature of the present invention is to provide a method that enables the determination that a subject has a predisposition for a bipolar disorder.

An additional feature of the present invention is to provide methods of identifying compounds that can be used to ultimately treat or prevent a bipolar disorder.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to methods of diagnosing, confirming a diagnosis of, and/or determining a predisposition for a bipolar disorder in a subject, and can include the following. An amount of at least one of the following biomarkers can be measured: isocitric acid in cerebrospinal fluid sample collected from the subject, cis-aconitic acid in cerebrospinal fluid sample collected from the subject, pyruvic acid in a serum sample collected from the subject, N-acetylglutamic acid in a serum sample collected from the subject, 2-oxoglutaric acid in a serum sample collected from the subject, β-alanine in a serum sample collected from the subject, arginine in a serum sample collected from the subject, serine in a serum sample collected from the subject, uric acid in a serum sample collected from the subject, and citric acid in a serum sample collected from the subject. The amount of the at least one biomarker can be compared with a control amount of the at least one biomarker in a corresponding sample collected from a subject without the bipolar disorder. An increase in the amount of isocitric acid, an increase in the amount of cis-aconitic acid, an increase in the amount of pyruvic acid, an increase in the amount of N-acetylglutamic acid, an increase in the amount of 2-oxoglutaric acid, a decrease in the amount of β-alanine, a decrease in the amount of arginine, a decrease in the amount of serine, an increase in the amount of uric acid, and a decrease in the amount of citric acid, in comparison to the control amount of the at least one biomarker can be indicative that the subject has the bipolar disorder or a predisposition for the bipolar disorder.

The present invention further relates to a method of identifying a compound for preventing and/or treating a bipolar disorder that can include the following. A eukaryotic cell can be contacted with a test compound. An expression level of an isocitric acid dehydrogenase 3 α-subunit gene, an isocitric acid dehydrogenase 3 β-subunit gene, or both can be measured in the cell and/or a culture containing the same. The expression level can be compared with a control expression level of the gene in an untreated eukaryotic cell. An increased expression level of the at least one gene compared to the control expression level can be indicative that the test compound is a candidate for preventing and/or treating a bipolar disorder. The method can also include selecting a test compound that decreased expression level of the at least one gene compared to the control expression level, and identifying the test compound as a candidate for preventing and/or treating a bipolar disorder.

The present invention also relates to a method of identifying a compound for preventing and/or treating bipolar disorder that can include the following. A test compound can be administered to an animal, for example, a non-human animal. An expression level of an isocitric acid dehydrogenase 3 α-subunit gene, an isocitric acid dehydrogenase 3 β-subunit gene, or both can be measured in a prefrontal cortex of the animal. The expression level can be compared with a control expression level of the at least one gene in a prefrontal cortex of an untreated animal. An increased level of the at least one gene compared to the control expression level can be indicative that the test compound is a candidate for preventing and/or treating bipolar disorder.

The present invention further relates to a method of identifying a compound for preventing and/or treating bipolar disorder that can include the following. A eukaryotic cell can be contacted with a test compound in a culture. An amount of at least one of the following biomarkers can be measured in the cell and/or culture: isocitric acid, cis-aconitic acid, pyruvic acid, N-acetylglutamic acid, 2-oxoglutaric acid, β-alanine, arginine, serine, uric acid, and citric acid. The amount of the at least one biomarker can be compared with a control amount of the at least one biomarker in a culture of untreated eukaryotic cells. A decrease in the amount of isocitric acid, a decrease in the amount of cis-aconitic acid, a decrease in the amount of pyruvic acid, a decrease in the amount of N-acetylglutamic acid, a decrease in the amount of 2-oxoglutaric acid, an increase in the amount of β-alanine, an increase in the amount of arginine, an increase in the amount of serine, a decrease in the amount of uric acid, and an increase in the amount of citric acid, in comparison to the control amount of the at least one biomarker can be indicative that the test compound is a candidate for preventing and/or treating bipolar disorder.

The present invention also relates to method of identifying a compound for preventing and/or treating bipolar disorder that can include the following. A test compound can be administered to an animal, for example, a non-human animal. An amount of at least one of the following biomarkers can be measured: isocitric acid in cerebrospinal fluid sample collected from the animal, cis-aconitic acid in cerebrospinal fluid sample collected from the animal, pyruvic acid in a serum sample collected from the animal, N-acetylglutamic acid in a serum sample collected from the animal, 2-oxoglutaric acid in a serum sample collected from the animal, β-alanine in a serum sample collected from the animal, arginine in a serum sample collected from the animal, serine in a serum sample collected from the animal, uric acid in a serum sample collected from the animal, and citric acid in a serum sample collected from the animal. The amount of the at least one biomarker can be compared with a control amount of at least one biomarker in a corresponding sample collected from an untreated animal. A decrease in the amount of isocitric acid, a decrease in the amount of cis-aconitic acid, a decrease in the amount of pyruvic acid, a decrease in the amount of N-acetylglutamic acid, a decrease in the amount of 2-oxoglutaric acid, an increase in the amount of β-alanine, an increase in the amount of arginine, an increase in the amount of serine, a decrease in the amount of uric acid, and an increase in the amount of citric acid, in comparison to the control amount of the at least one biomarker can be indicative that the test compound is a candidate for preventing and/or treating bipolar disorder.

It is to be understood that both the foregoing general description and the following detailed description are exemplary and explanatory only and intended to provide a further explanation of the present invention, as claimed.

DETAILED DESCRIPTION OF THE PRESENT INVENTION

Figure 1:
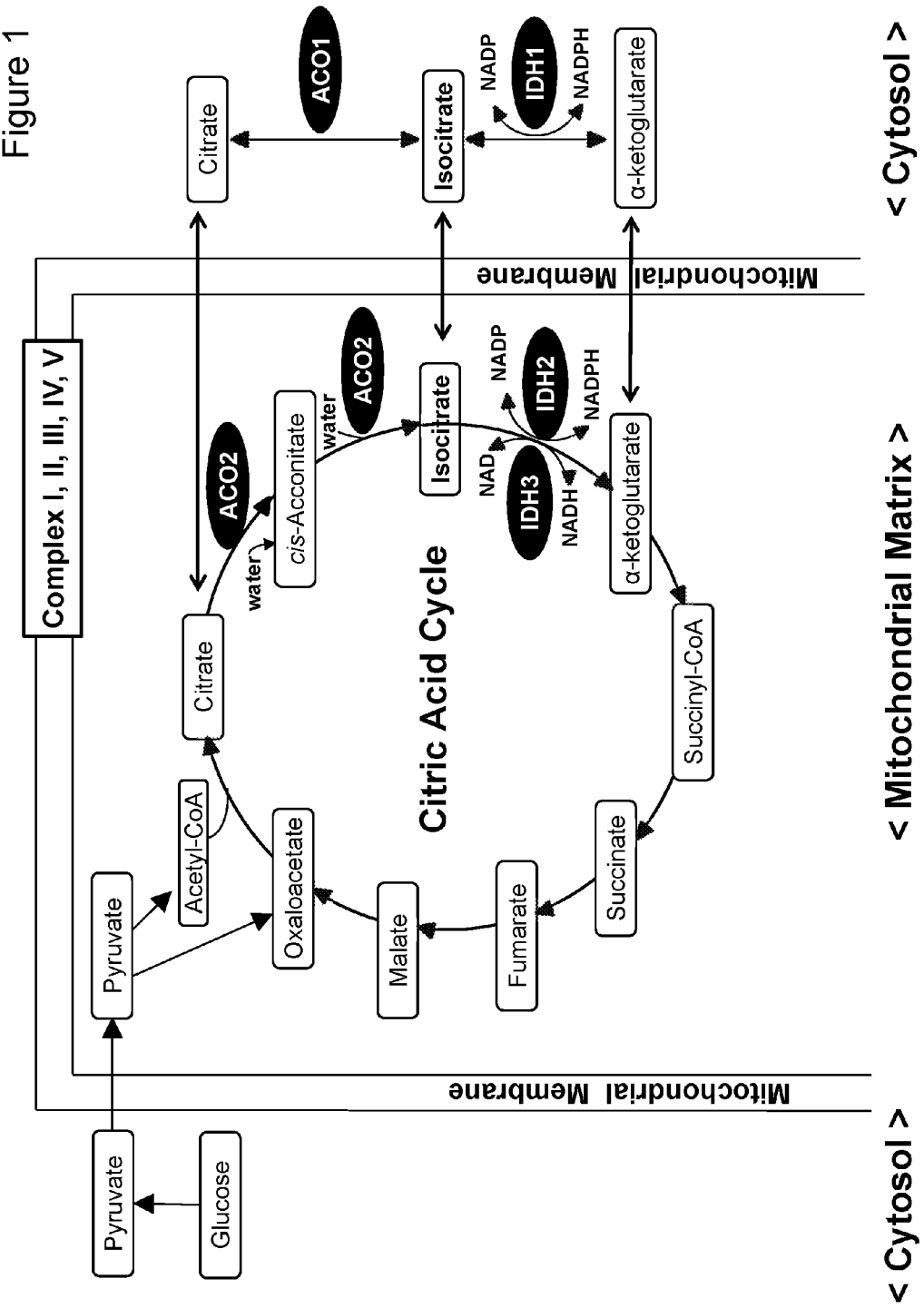
FIG. 1 is a schematic diagram of a metabolic pathway highlighting citrate and isocitrate in the citric acid cycle that occurs in the mitochondrial matrix and in the cytosol
Figure 2:
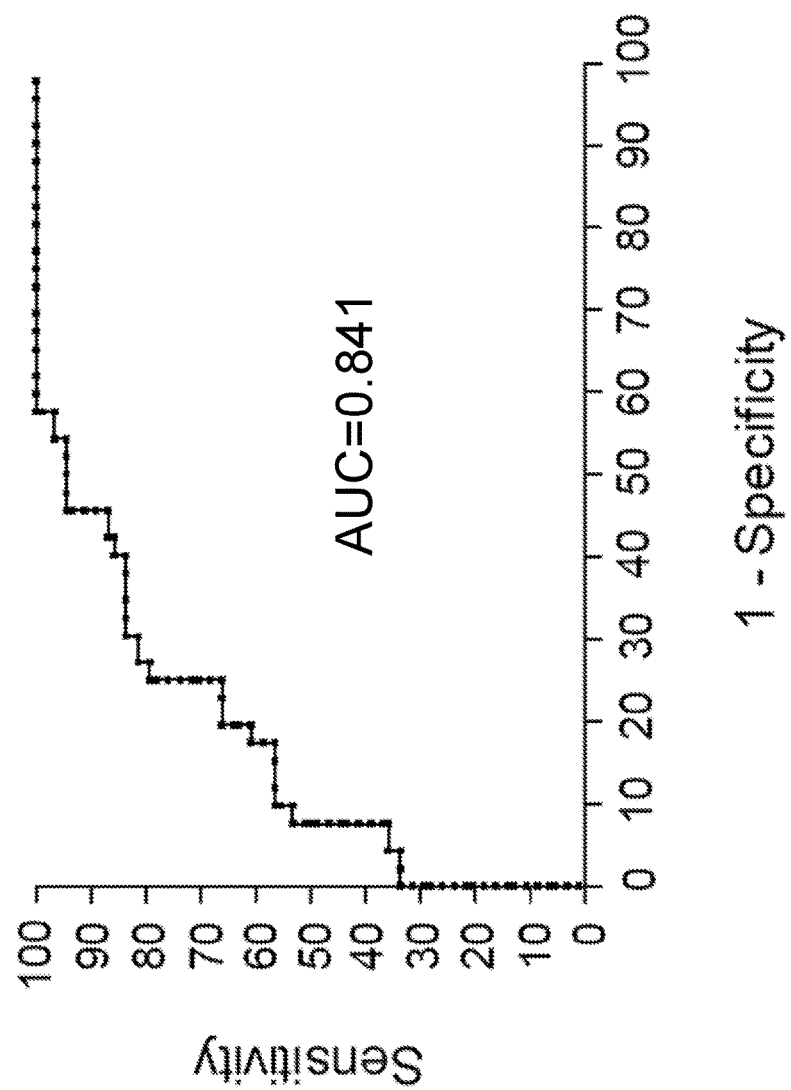
FIG. 2 is a graph displaying a receiver-operating characteristics (ROC) curve and area under the curve (AUC).

The present invention relates to methods of diagnosing, confirming a diagnosis of, or determining a predisposition for a bipolar disorder in a subject, and can include the following. An amount of at least one of the following biomarkers can be measured: isocitric acid in cerebrospinal fluid sample collected from the subject, cis-aconitic acid in cerebrospinal fluid sample collected from the subject, pyruvic acid in a serum sample collected from the subject, N-acetylglutamic acid in a serum sample collected from the subject, 2-oxoglutaric acid in a serum sample collected from the subject, β-alanine in a serum sample collected from the subject, arginine in a serum sample collected from the subject, serine in a serum sample collected from the subject, uric acid in a serum sample collected from the subject, and citric acid in a serum sample collected from the subject. The amount of the at least one biomarker can be compared with a control amount of the at least one biomarker in a corresponding sample collected from a subject without the bipolar disorder. An increase in the amount of iso citric acid, an increase in the amount of cis-aconitic acid, an increase in the amount of pyruvic acid, an increase in the amount of N-acetylglutamic acid, an increase in the amount of 2-oxoglutaric acid, a decrease in the amount of β-alanine, a decrease in the amount of arginine, a decrease in the amount of serine, an increase in the amount of uric acid, and a decrease in the amount of citric acid, in comparison to the control amount of the at least one biomarker can be indicative that the subject has the bipolar disorder or a predisposition for the bipolar disorder. The subject can be a human subject or an animal model of a bipolar disorder.

Any biomarker alone or a combination of biomarkers listed can be used, and optionally can be combined with one or more additional biomarkers not listed. For example, the at least one biomarker can include isocitric acid in a cerebrospinal fluid sample collected from the subject. The isocitric acid can be measured alone or in combination with one or more additional biomarkers whether or not listed. For example, isocitric acid in a cerebrospinal fluid sample and serine in a serum sample collected from the subject can both be measured and compared with controls and/or with each other. A ratio of two or more biomarkers measured can be calculated and compared with a control ratio. The at least one biomarker measured and compared can include in combination, for example, at least one of the biomarkers collected from cerebrospinal fluid and at least one of the biomarkers collected from serum of the subject. Any suitable combination of the biomarkers can be measured, alone, or in combination with one or more further biomarkers. At least two, three, four, five, six, seven, eight, nine, ten, or more biomarkers in combination can be measured and compared with corresponding controls. For example, the following biomarkers can be measured in combination: isocitric acid in cerebrospinal fluid sample collected from a subject, cis-aconitic acid in cerebrospinal fluid sample collected from a subject, serine in a serum sample collected from the subject, uric acid in a serum sample collected from the subject, and citric acid in a serum sample collected from the subject. For example, the following biomarkers can be measured in combination: pyruvic acid in a serum sample collected from the subject, N-acetylglutamic acid in a serum sample collected from the subject, 2-oxoglutaric acid in a serum sample collected from the subject, β-alanine in a serum sample collected from the subject, arginine in a serum sample collected from the subject; and serine in a serum sample collected from the subject.

The methods of the present invention can use existing biomarker data, a previously collected sample, and/or include collecting a sample from the subject. The methods can include contacting a human subject directly or indirectly. The methods can be devoid of direct contact with any human subject. Cerebrospinal fluid can be collected from the subject, serum can be collected from the subject, or both. One or more purification steps can be performed on a sample before measuring the amounts of the one or more biomarkers present. Alternatively, amounts can be measured without purification. Control samples or amounts of biomarkers can be based on one or more control subjects. The collecting can be performed at any suitable time. For example, a sample can be collected when the subject is euthymic, during a manic episode, during a depressive episode, and/or at any point during a bipolar episode. More than one sample can be collected and/or measured. Multiple measurements can be averaged before comparison with a control amount. A control amount can also be based on an average. An average can be, for example, an arithmetic or geometric mean, median, and/or mode. The control amount can be a particular amount or a range. In accordance with the methods of the present invention, the increase and/or decrease of a biomarker relative to a control can be about at least 0.001%, 0.01%, 0.1%, 0.5%, 1.0%, 2.0%, 3.0%, 4.0%, 5.0%, 10%, 15%, 20%, 25%, 40%, 50%, 60%, 75%, 90%, or 100%, or less than 0.001%, or greater than 100%. The at least one biomarker can include an amount of a metabolite and/or an expression level of a gene.

The subject tested need not have been previously diagnosed with a bipolar disorder or any other psychological ailment. Alternatively, the subject can have been previously and/or concurrently diagnosed with one or more psychological ailments, for example, a bipolar disorder. The subject can have had at least one bipolar episode, at least one manic episode, at least one hypomanic episode, at least one depressive episode, or any combination thereof. One or more additional diagnostic tests for the bipolar disorder can be performed before, concurrent with, and/or after the biomarker-based test. The additional tests can also be a biomarker based test or can be a diagnostic test that is not based on a biomarker. For example, the other diagnostic test can be an interview-based test. A clinical assessment instrument can be used as the additional diagnostic test, for example, the Affective Disorder Evaluation (ADE), developed for the Systematic Treatment Enhancement Program of Bipolar Disorder (STEP-BD) performed consistent with the description in Sachs et al., Biol Psychiatry. 2003; 53(1):1028-1042. A subject not previously diagnosed with a bipolar disorder can have at least one biological family member that has been diagnosed with a bipolar disorder, for example, a father, a mother, a sister, a brother, a grandmother, a grandfather, a son, a daughter, and/or a cousin.

The bipolar disorder tested for can be any bipolar disorder or combination of bipolar disorders. For example, the bipolar disorder can be a bipolar type I disorder, a bipolar type II disorder, rapid-cycling bipolar disorder, bipolar disorder not otherwise specified, cyclothymia, or any combination thereof. The bipolar disorder can be a bipolar disorder based on the criteria defined in the Diagnostic and Statistical Manual (DSM)-IV or V. The severity of the bipolar disorder can be rated using the Clinical Global Impression (CGI) rating scales and Global Assessment of Functioning (GAF). Bipolar disorder I disorder can be characterized by manic or mixed episodes that last at least seven days, or by manic symptoms that are so severe that the person needs immediate hospital care. Bipolar disorder I can also include depressive episodes, typically lasting at least 2 weeks. Bipolar disorder II can be characterized by a pattern of depressive episodes and hypomanic episodes, but without full-blown manic or mixed episodes. Bipolar disorder not otherwise specified can be characterized by one or more symptoms of bipolar disorder I and/or II. Bipolar disorder not otherwise specified need not meet all the criteria of bipolar disorder I and/or II, but with symptoms that are still outside of a normal range of behavior. Cyclothymia or cyclothymic disorder is a milder form of bipolar disorder and need not meet all the criteria of bipolar disorder I and/or II. Cyclothymia can be characterized by episodes of hypomania as well as mild depression for at least 2 years. Rapid-cycling bipolar disorder can be characterized by four or more episodes of major depression, mania, hypomania, or mixed states, all within a year. A bipolar disorder can include one or more of the following symptoms: mania, hypomania, depression, euphoria, lack of concentration, rapid and/or loud speech, hyperactivity, insomnia, shorter sleep periods, inflated self-image, excessive spending, hypersexuality, substance abuse, or any combination thereof.

The method can be performed independent of any therapeutic regimen or in combination with a therapeutic regimen. The method can include administering at least one bipolar medication to the subject. The medication can be administered before, during, and/or after collecting, measuring, and/or comparing the at least one biomarker. Any suitable medication can be used. The bipolar medication can treat at least one symptom of mania, depression, or both. For example, the at least one bipolar medication can include lithium, valproic acid, carbamazepine, oxcarbazepine, lamotrigine, lurasidone, divalproex, or any salt thereof, or any combination thereof. The bipolar medication can include at least one mood stabilizer, at least one antidepressant, at least one antipsychotic medication, at least one anti-seizure medication, at least one anti-convulsant medication, at least one benzodiazepine, or any combination thereof. Examples of mood stabilizers can include lithium, divalproex sodium, carbamazepine, valproic acid, lamotrigine, oxcarbazepine, or any combination thereof. Examples of antipsychotics can include olanzapine, aripipazole, risperidone, ziprasidone, clozapine, lurasidone, or any combination thereof. Examples of anti-seizure and anti-convulsant medications can include carbamazepine, clonazepam, clorazepate dipotassium, diazepam, ethosuximide, ethotoin, felbamate, fosphenytoin, gabapentin, lamotrigine, levetircetam, lorazepam, mephenytoin, mephobarbital, oxycarbazepine, pentobarbital, phenytoin, primidone, tiagabine, topiramate, trimethadiione, valproic acid, or any combination thereof. Examples of antidepressants can include fluoxetine, paroxetine, sertraline, citalopram, escitalopram, bupropion, tricyclics, tetracyclics, monoamine oxidase inhibitors, or any combination thereof. Examples of benzodiazepines can include alprazolam, chlordiazepoxide, clorazepate, diazepam, estazolam, flurazepam, lorazepam, oxazepam, prazepam, quazepam, temazepam, triazolam, or any combination thereof. Any salt or combination of salts of any active pharmaceutical ingredient can be employed. A non-pharmaceutical therapy, for example, electroconvulsive therapy and/or deep brain stimulation, can be used instead of or in addition to at least one (pharmaceutical) medication.

The present invention further relates to a method of identifying a compound or combination of compounds for preventing and/or treating a bipolar disorder that can include the following. A eukaryotic cell can be contacted with a test compound. An expression level of an isocitric acid dehydrogenase 3 α-subunit gene, an isocitric acid dehydrogenase 3 η-subunit gene, or both can be measured in the cell and/or a culture containing the same. The expression level can be compared with a control expression level of the gene in an untreated eukaryotic cell. An increased expression level of the at least one gene compared to the control expression level can be indicative that the test compound is a candidate for preventing and/or treating a bipolar disorder. The method can also include selecting a test compound that decreased expression level of the at least one gene compared to the control expression level, and identifying the test compound as a candidate for preventing and/or treating a bipolar disorder. The expression levels of one or more genes in addition to that of an isocitric acid dehydrogenase 3 α-subunit gene and/or an isocitric acid dehydrogenase 3 β-subunit gene can also be analyzed. The identified compound can be administered to a subject. The subject can have been diagnosed with a bipolar disorder or a predisposition for a bipolar disorder. A diagnostic test can then be performed on the subject. For example, the amount of at one biomarker can be measured in a sample from the subject. The amount of at least one biomarker in the sample can be compared with a control amount of the at least one marker, wherein an increase or decrease of the amount of the at least one biomarker is indicative that the bipolar disorder has been treated or prevented.

Any suitable cell type can be used for the treated and untreated (control) cells. It is advantageous to use a eukaryotic cell, because eukaryotic cells typically include one or more mitochondria. However, artificial constructs of cells that do not ordinarily contain mitochondria can be used, for example, bacteria or other cells modified to express an isocitric acid dehydrogenase 3 α-subunit gene, an isocitric acid dehydrogenase 3 β-subunit gene, or both. Any kind or combination of eukaryotic cells can be used. For example, the eukaryotic cell can be derived from a unicellular or multicellular organism. The eukaryotic cell can be, for example, a yeast. The eukaryotic cell can be derived from an animal, for example an invertebrate or vertebrate. The eukaryotic cell can include one or more type of mammalian cell, for example, one or more kinds of murine, rat, hamster, primate, or human cells. The cell can be derived from any suitable tissue or combination of tissues. The cell can be derived any suitable organ or system, for example, the brain or central nervous system. The cell can be derived from any part or parts of the brain, for example, the hippocampus or the prefrontal cortex, for example, the dorsolateral prefrontal cortex. Any kind or combination of brain cell can be used, for example, a neuron, a glial cell, or both. Cells can be unmodified from their natural state or modified in one or more way using any suitable technique, for example, genetically modified. The cells can be genetically engineered, for example, to reduce expression of the isocitric acid dehydrogenase 3 α-subunit gene, the isocitric acid dehydrogenase 3 β-subunit gene, or both. One or more genes can be modified. One or more alleles for each gene can be used. The cells can be immortalized. Any suitable cell line can be used. A normal and/or cancerous cell line can be used.

Any animal or combination of animals can be used in the diagnostic, screening, and treatment methods of the present invention. The animal can be a non-human animal. The animal can be a mouse, a rat, a hamster, a gerbil, a rabbit, a guinea pig, a cat, a dog, a sheep, a goat, a pig, a horse, a cow, a monkey, an ape, a rhesus monkey, a chimpanzee, a baboon, or any combination thereof. The animal can be a human. The non-human animal can be a model for one or more bipolar disorders. The non-human animal can be genetically engineered. For example, the non-human animal can be genetically engineered to add a gene and/or alter a gene. One allele can be exchanged for another. A gene from one species can be used to replace a counterpart or homologous gene in another species. The non-human animal can be genetically engineered to alter the level of one or more biomarker. For example, the non-human animal can be genetically engineered to alter the amount of one or more metabolite, and/or the expression level of one or more gene. Homologous recombination and/or any other suitable technique can be employed.

The screening methods of the present invention can further include selecting a test compound that has a decreased expression level of the at least one gene compared to the control expression level. The screening methods of the present invention can further include identifying the test compound as a candidate for preventing and/or treating a bipolar disorder. Screening methods employing cells or animals can be used independently or in combination. For example, a test compound identified as a candidate using a cellular assay can be subsequently tested or confirmed in an animal, or vice versa. That is, the test compound can be determined as a candidate for preventing and/or treating a bipolar disorder, and then administered to an animal. An expression level of the isocitric acid dehydrogenase 3 α-subunit gene, the isocitric acid dehydrogenase 3 β-subunit gene, or both can be measured in a prefrontal cortex of the animal with the understanding that the version of the genes may differ due to differences in species between the animal and the animal or human from which the cell is derived. The genes can still be counterparts and optionally have a high percent identity, for example, at least 75%, 85%, 90%, 95%, or 98% identical. The expression level of the at least one gene can then be compared with a control expression level of the at least one gene in a prefrontal cortex of an untreated animal, wherein an increased level of the at least one gene compared to the control expression level is indicative that the test compound is a bipolar disorder therapeutic. When a cellular and an animal test are combined, they may differ with respect to biomarker or biomarkers tested. For example, the cellular assay can be based on gene expression and the animal assay on at least one metabolite biomarker, or vice versa. Depending on the particular gene or allele, the indicator for screening can be an increase or decrease in expression.

Any of the screening methods of the present invention can be practiced using a single test compound or a combination of test compounds. For example, a combination of two, three, four, five, six, or more test compounds can be employed. One or more test compounds can be used in combination with one or more known bipolar medications as part of a screening assay. A combination of test compounds can be tested for synergy using the screening assays of the present invention. A combination of one or more test compounds and one or more known bipolar medications can be tested for synergy using the screening assays of the present invention. Synergy can refer to an effect greater than if either compound were used alone. Synergy can be more than additive, for example, the effect of treating and/or preventing a bipolar disorder can be more than the sum of the individual effects of the test compounds. A test compound can have no effect on a bipolar disorder on its own, but can enhance the efficacy one or more other test compounds or one or more known bipolar medications, when combined with such compounds or medications.

The present invention also relates to a method of identifying a compound or combination of compounds for preventing and/or treating bipolar disorder that can include the following. A test compound can be administered to an animal. An expression level of an isocitric acid dehydrogenase 3 α-subunit gene, an isocitric acid dehydrogenase 3 β-subunit gene, or both can be measured in a prefrontal cortex of the animal. The expression level can be compared with a control expression level of the at least one gene in a prefrontal cortex of an untreated animal. An increased level of the at least one gene compared to the control expression level can be indicative that the test compound is a candidate for preventing and/or treating bipolar disorder. The animal can be genetically engineered to reduce expression of the isocitric acid dehydrogenase 3 α-subunit gene, the isocitric acid dehydrogenase 3 β-subunit gene, or both. The method can also include selecting a test compound that has a decreased expression level of the at least one gene compared to the control expression level. The method can further include identifying the test compound as a candidate for preventing and/or treating a bipolar disorder.

The present invention further relates to a method of identifying a compound or a combination of compounds for preventing and/or treating bipolar disorder that can include the following. A eukaryotic cell can be contacted with a test compound in a culture. An amount of at least one of the following biomarkers can be measured in the cell and/or culture, isocitric acid, cis-aconitic acid, pyruvic acid, N-acetylglutamic acid, 2-oxoglutaric acid, β-alanine, arginine, serine, uric acid, and citric acid. The amount of the at least one biomarker can be compared with a control amount of the at least one biomarker in a culture of untreated eukaryotic cells. A decrease in the amount of isocitric acid, a decrease in the amount of cis-aconitic acid, a decrease in the amount of pyruvic acid, a decrease in the amount of N-acetylglutamic acid, a decrease in the amount of 2-oxoglutaric acid, an increase in the amount of β-alanine, an increase in the amount of arginine, an increase in the amount of serine, a decrease in the amount of uric acid, and an increase in the amount of citric acid, in comparison to the control amount of the at least one biomarker can be indicative that the test compound is a candidate for preventing and/or treating bipolar disorder. The at least one biomarker can include isocitric acid. The cell can be genetically engineered to reduce expression of isocitric acid dehydrogenase 3 β-subunit gene, a isocitric acid dehydrogenase 3 β-subunit gene, or both. The method can also include selecting a test compound that increased or decreased expression level of the at least one gene as specified compared to the control expression level. The method can further include identifying the test compound as a candidate for preventing and/or treating a bipolar disorder. Cell-based assays of the present invention can include sampling from the cells, the cell culture or both. Cells can be cultured as individual cells, colonies, tissues, and/or organs. Cells and cell constructs can be naturally occurring and/or artificially constructed.

The present invention also relates to a method of identifying a compound or combination of compounds for preventing and/or treating bipolar disorder that can include the following. A test compound can be administered to an animal. An amount of at least one of the following biomarkers can be measured: isocitric acid in cerebrospinal fluid sample collected from the animal, cis-aconitic acid in cerebrospinal fluid sample collected from the animal, pyruvic acid in a serum sample collected from the animal, N-acetylglutamic acid in a serum sample collected from the animal, 2-oxoglutaric acid in a serum sample collected from the animal, β-alanine in a serum sample collected from the animal, arginine in a serum sample collected from the animal, serine in a serum sample collected from the animal, uric acid in a serum sample collected from the animal, and citric acid in a serum sample collected from the animal. The amount of the at least one biomarker can be compared with a control amount of at least one biomarker in a corresponding sample collected from an untreated animal. A decrease in the amount of isocitric acid, a decrease in the amount of cis-aconitic acid, a decrease in the amount of pyruvic acid, a decrease in the amount of N-acetylglutamic acid, a decrease in the amount of 2-oxoglutaric acid, an increase in the amount of β-alanine, an increase in the amount of arginine, an increase in the amount of serine, a decrease in the amount of uric acid, and an increase in the amount of citric acid, in comparison to the control amount of the at least one biomarker can be indicative that the test compound is a candidate for preventing and/or treating bipolar disorder. The at least one biomarker can include isocitric acid. The animal can be genetically engineered to reduce expression of isocitric acid dehydrogenase 3 β-subunit gene, a isocitric acid dehydrogenase 3 β-subunit gene, or both.

The methods of the present invention can employ any technique, apparatus, or combination thereof to measure a biomarker such as a metabolite and/or gene expression. For example, capillary electrophoresis time-of-flight mass spectrometry (CE-TOFMS) and/or high performance liquid chromatography (HPLC) can be used to measure metabolites. Metabolites can be measured using an enzyme-linked immunosorbent assay (ELISA). Gene expression can be measured, for example, by using real-time quantitative RT-PCR analysis and/or a gene chip.

The present invention includes compounds and combination of compounds identified for preventing and/or treating a bipolar disorder using one or more methods of the present invention. Compounds can be formulated with one or more additional pharmaceutically acceptable excipients. An identified compound can be administered to a subject to prevent and/or treat a bipolar disorder. Preventing or treating a bipolar disorder can include eliminating and/or diminishing one or more symptoms of a bipolar disorder. After administering an identified compound to a subject, a diagnostic test of the present invention can be performed. Methods of the present invention include performing a diagnostic test of the invention to determine or confirm the efficacy of a pharmaceutical compound generally or to sample or track the efficacy of a pharmaceutical compound in a particular subject in treating or preventing a bipolar disorder. For example, administration of a bipolar disorder pharmaceutical to a subject can be sampled in a single measurement or tracked over time to determine if one or more biomarkers decrease or increase over time. If a particular pharmaceutical compound does not alter the level of the one or more biomarkers to a or towards a level of the biomarkers in a subject that does not suffer from a bipolar disorder, an alternative or additional medication can be administered.

The present invention includes kits suitable for carrying out diagnostic or screening assays. For example, a kit can include instructions for conducting one or more methods according to the present invention. A kit can include one or more controls and/or control data. A kit can include one or more test compounds or candidate compounds. A kit can include one or more cell types for use in assaying test compounds for use in treating or preventing a bipolar disorder. A kit can include one or more containers for holding and/or purifying a sample. A kit can include one or more reagents to assist in the detection and quantification of one or more biomarker. For example, a kit can include a plate suitable for an ELISA-type assay and/or a gene chip containing one or more nucleic acids.

The present invention will be further clarified by the following examples, which are intended to be exemplary of the present invention.

In the following examples, metabolomics assays were performed using CE-TOFMS of CSF samples of mood-stabilized BD patients and age-matched healthy controls. Gene expression analyses in postmortem brain samples and genetic association analyses of the genes relevant to the substance identified by CSF metabolomics were also performed. In order to examine the effect of medication on metabolites, metabolomics characterization of CSF samples from rats chronically treated with lithium (Li) or valproic acid (VPA) were also performed.

Data from human samples are presented as mean±standard deviation (SD). Statistical analysis was performed using SAS software version 9.3 (SAS Institute, Cary, N.C.). Analyses of metabolites between control and BD groups were performed using unpaired t-tests and Wilcoxon rank sum tests. A logistic regression model with a stepwise selection method was used for the multivariate analysis and multiple regression analysis (consistent with description in Allen et al., Technometrics. 1974; 16(1):125-127; and Miller et al., Chapman and Hall. 1974, which are incorporated in their entireties by reference herein). Internal validation of the logistic regression models was performed using the Hosmer-Lemeshow goodness-of-fit test, in which a P value greater than 0.1 indicates a good fit (consistent with the description in Hunziker et al., Crit. Care Med. 2011; 39(7): 1670-1674, which is incorporated in its entirety by reference herein), and the performance was evaluated by the jack-knife method (a performance evaluation method in which a measured value is predicted from the n−1 observations, removing the own predicted observation) (consistent with the description in Wadelius et al., Blood. 2009; 113(4):784-792, which is incorporated in its entirety by reference herein). The Mann-Whitney U test (two-tailed) was used to evaluate changes in expression levels of the ACO and IDH genes between control and BD groups. Rat data are presented as mean±SD. To determine the effects of drug treatment, a one-way ANOVA, followed by the post hoc Dunnett's test was used. P values of less than 0.05 for two-tailed tests were considered statistically significant.

EXAMPLES

Example 1

This example demonstrates that the levels of various metabolites in cerebrospinal fluid (CSF) can be used to predict a diagnosis of bipolar disorder (BD) in human patients. For example, levels of isocitrate were found to positively correlate with BD.

The BD patients were recruited from the St. Goran bipolar project, enrolling patients from the bipolar unit at the Northern Stockholm Psychiatric Clinic, Stockholm, Sweden. Work-up and diagnostic assessments were performed consistent with the descriptions in Jakobsson et al., Neuropsychopharmacology. 2014; 39(10):2349-2356; Ryden et al., J. Neural Transm. 2009; 116(2):1667-1674; and PÅlsson et al., Eur. Neuropsychopharmacol., 2015; 25(1):133-140, which are incorporated in their entireties by reference herein. The key clinical assessment instrument used was the Affective Disorder Evaluation (ADE), developed for the Systematic Treatment Enhancement Program of Bipolar Disorder (STEP-BD) (consistent with the description in Sachs et al., Biol. Psychiatry. 2003; 53(1):1028-1042, which is incorporated in its entirety by reference herein). The full diagnostic assessment was based on all available sources of information including patient interview, case records and, if possible, interviews with the next of kin. To reduce inter-rater bias, a best-estimate diagnostic decision based on all information available at admission was made at a diagnostic case-conference by a consensus panel of experienced board certified psychiatrists (n=2-5) specialized in bipolar disorder (BD).

The general criteria for inclusion were: 1) age of at least 18 years and 2) meeting the Diagnostic and Statistical Manual (DSM)-IV criteria for bipolar spectrum disorder (i.e., type I, type II, and not otherwise specified). Information regarding age, sex, number of lifetime manic/hypomanic/depressive/total episodes, duration of illness (defined as years since first hypomanic or manic episode), body mass index (BMI), and previous psychotic episodes was collected. The severity of BD was rated using the Clinical Global Impression (CGI) rating scales and Global Assessment of Functioning (GAF). For ethical reasons, patients continued to take their prescribed medications at the time of CSF sampling.

Population-based controls were randomly selected by Statistics Sweden (SCB) and contacted by mail. Given an expected response rate of 1:7, seven invitations were sent out per enrolled subject. Fourteen percent of the invited controls responded to the invitation, and were subjected to a preliminary telephone screening by a research nurse to exclude severe mental health conditions, neurological diseases, and substance abuse. Eligible persons were scheduled for a one-day comprehensive assessment where they underwent a psychiatric interview by experienced clinicians using the Mini-International Neuropsychiatric Interview (M.I.N.I.) to exclude psychiatric disorders (consistent with the description in Sheehan et al., J. Clin. Psychiatry. 1998; 59(Suppl 20):22-33, which is incorporated in its entirety by reference herein). Substance abuse was screened for at the telephone interview by the nurse, in the psychiatric interview, by the Alcohol Use Disorders Identification Test (AUDIT) and the Drug Use Disorders Identification Test (DUDIT), as well as by determining serum levels of carbohydrate-deficient transferrin (CDT) (consistent with the description in Saunders et al., Addiction. 1993; 88(6):791-804, which is incorporated in its entirety by reference herein). Overconsumption of alcohol as revealed by CDT or responses indicating large consumption (>8 standard drinks per time more than 2 times per week), and/or amnesia and/or loss of control more than once per month resulted in the exclusion of these individuals from the study. Other exclusion criteria were neurological conditions other than mild migraines, untreated endocrinological disorders, pregnancy, dementia, recurrent depressive disorder, and suspected severe personality disorders (based on interview and the Structured Clinical Interview for DSM (SCID-II) screen personality assessment), and a family history of schizophrenia or BD in first-degree relatives.

The study was approved by the Regional Ethics Committee in Stockholm and conducted in accordance with the latest Helsinki Protocol. All patients and controls consented orally and in writing to participate in the study. Informed consent was obtained during a euthymic period (that is, during a time period when patients did not meet criteria for a depressive or manic episode). All patients were capable of freely giving fully informed consent, as determined by the physicians who enrolled the patients. A total of 54 male BD patients and 40 male healthy controls were included (Table 1).

TABLE 1

Characteristics of the participants

|  | Controls | | Bipolar disorder (BD) | |
| --- | --- | --- | --- | --- |
| Sex (male) | 40[a] | | 54 | |
|  | Median | IQR | Median | IQR |
| Age (years) | 36 | 21-74 | 41 | 20-73 |
| BMI | 25.7 | 18.3-32.5 | 24.1 | 19.6-32.5 |

| Diagnosis | N | % |
| --- | --- | --- |
| Bipolar disorder type I (BP I) | 31 | 57.4 |
| Bipolar disorder type II (BP II) | 17 | 31.5 |
| Not otherwise specified (NOS) | 6 | 11.1 |

| Clinical data | Median | IQR |
| --- | --- | --- |
| Age first symptoms | 20 | 5-58 |
| Depressive episodes[c] | 6 | 0-60 |
| Hypomanic episodes[b] | 6 | 0-40 |
| Manic episodes[b] | 1 | 0-10 |
| Mixed episodes[b] | 0 | 0-25 |
| GAF[b] | 70 | 21-90 |
| MADRS[d] | 4 | 0-44 |
| YMRS[e] | 1 | 0-11 |
| No of episodes[b] | 18 | 1-80 |

|  | N | % |
| --- | --- | --- |
| Psychosis episodes[b] | 25 | 46.3 |
| Medication | | |
| Mood stabilizer | 44 | 81.5 |
| Lithium (Li) | 34 | 63 |
| Anticonvulsants | 19 | 35.2 |
| Valproate (VPA) | 7 | 13 |
| Lamotrigine | 12 | 22.2 |
| Antidepressants | 20 | 37 |

TABLE 1-continued

Characteristics of the participants

|  | Controls | Bipolar disorder (BD) |
|---|---|---|
| Anxiolytics |  | 11 20.4 |
| Antipsychotics |  | 16 29.6 |

[a] Missing data for 1 individual in the control group
[b] Missing data for 1 individual in the patient group
[c] Missing data for 2 individual in the patient group
[d] Missing data for 10 individual in the patient group
[e] Missing data for 11 individual in the patient group
IQR: Interquartile Range
GAF: Global Assessment of Functioning
MADRS: Montgomery-Åsberg Depression Rating Scale
YMRS: Young Mania Rating Scale CSF sampling (lumbar puncture) was performed when the participants were euthymic. Sampling occurred between 9.00 and 10.00 a.m. after an overnight fast. To collect CSF, the spinal needle was inserted into the L3/L4 or L4/L5 interspace and a standardized volume of 12 mL CSF was collected in a polypropylene tube, gently inverted to avoid gradient effects, and divided into 1.0-1.6 mL aliquots in polypropylene tubes. The aliquoted CSF samples were stored at ~80° C. pending analysis at the Biobank at Karolinska Institute, Stockholm, Sweden. An identical procedure was performed for the controls. The samples were stored at ~80° C. until delivered by courier mail, frozen on dry ice, to Chiba University, Japan for metabolomics analysis. This study was approved by Research Ethics Committee of the Graduate School of Medicine, Chiba University.

Metabolomic analyses of CSF samples from healthy controls and BD patients were performed using the CE-TOFMS at Human Metabolome Technologies (Yamagata, Japan). In this study, 116 major metabolic compounds from various pathways (glycolytic system, pentose phosphate pathway, citric acid cycle, urea cycle, polyamine-creatine metabolism pathway, purine metabolism pathway, glutathione metabolism pathway, nicotinamide metabolism pathway, choline metabolism pathway and diverse amino acid metabolism pathway) were selected for metabolomics analysis (Tables 2 and 3).

TABLE 2

List of all metabolites and pathways

| Metabolites | Pathway |
|---|---|
| 2,3-Diphosphoglyceric acid | Glycolysis |
| 2-Hydroxyglutaric acid | Glutatione Metabolism |
| 2-Oxoglutaric acid | Citric acid cycle |
| 2-Oxoisovaleric acid | BCAA Metabolism |
| 2-Phosphoglyceric acid | Glycolysis |
| 3-Phosphoglyceric acid | Glycolysis |
| 6-Phosphogluconic acid | Nicotinamides, Pentose Phosphate Pathway |
| Acetoacetyl CoA | BCAA Metabolism, Lipid Metabolism |
| Acetyl CoA | Glycolysis, Citric acid cycle |
| Adenine | Purine Metabolism |
| Adenosine | Purine Metabolism |
| Adenylosuccinic acid | Urea cycle |
| Adenosine diphosphate (ADP) | Purine Metabolism |
| ADP-ribose | Pentose Phosphate Pathway |
| Alanine (Ala) | Glycolysis |
| Adenosine monophosphate (AMP) | Purine Metabolism |
| Arginine (Arg) | Urea Cycle |
| Argininosuccinic acid | Urea Cycle |
| Asparagine (Asn) | Urea Cycle, Glycolysis |
| Aspartic acid (Asp) | Urea Cycle, Glycolysis |
| Adenosine triphosphate (ATP) | Purine Metabolism |
| Betaine | Choline Metabolism |
| Betaine aldehyde | Choline Metabolism |
| cyclic AMP (cAMP) | Purine Metabolism |
| Carbamoylphosphate | Urea Cycle |
| Carnitine | Lipid Metabolism |
| Carnosine | Glutatione Metabolism |
| cyclic GMP (cGMP) | Purine Metabolism |
| Choline | Choline Metabolism |
| cis-Aconitic acid | Citric acid cycle |
| Citric acid | Citric acid cycle |
| Citrulline | Urea Cycle |
| CoA | Citric acid cycle, Urea Cycle, Glycolysis, BCAA Metabolism, Lipid metabolism |
| Creatine | Polyamines & Creatine |
| Creatinine | Polyamines & Creatine |
| Cysteine (Cys) | Lipid Metabolism, Glutatione Metabolism, Methylation, Transsulfuration pathway |
| Cystathionine | Methylation, Transsulfuration pathway |
| Dihydroxyacetone phosphate | Glycolysis |
| Erythrose 4-phosphate | Pentose Phosphate Pathway |
| Folic acid | Glutatione Metabolism, Met Cycle |
| Fructose 1,6-diphosphate | Glycolysis |
| Fructose 1-phosphate | Glycolysis |
| Fructose 6-phosphate | Glycolysis, Pentose Phosphate Pathway |
| Fumaric acid | Citric acid cycle |
| Galactose 1-phosphate | Pentose Phosphate Pathway |
| Guanosine diphosphate (GDP) | Purine Metabolism |
| Glutamine (Gln) | Glutatione Metabolism |

TABLE 2-continued

List of all metabolites and pathways

| Metabolites | Pathway |
| --- | --- |
| Glutamic acid (Glu) | Glutatione Metabolism, Urea Cycle |
| Glucose 1-phosphate | Glycolysis, Pentose Phosphate Pathway |
| Glucose 6-phosphate | Glycolysis |
| Glutathione (GSH) | Glutatione Metabolism |
| Glutathione (GSSG) | Glutatione Metabolism |
| Glycine (Gly) | Choline Metabolism, Glutatione Metabolism |
| Glyceraldehyde 3-phosphate | Glycolysis, Pentose Phosphate Pathway |
| Glycerol 3-phosphate | Glycolysis, Lipid Metabolism |
| Glycolic acid | Glycolysis, Choline Metabolism |
| Glyoxylic acid | Choline Metabolism |
| Guanosine monophosphate (GMP) | Purine Metabolism |
| Guanosine triphosphate (GTP) | Purine Metabolism |
| Guanine | Purine Metabolism |
| Guanosine | Purine Metabolism |
| Histidine (His) | Glutatione Metabolism |
| HMG CoA | Lipid Metabolism, BCAA Metabolism |
| Homocysteine | Methionine Cycle, Methylation, Transsulfuration pathway |
| Homoserine | Citric acid cycle, Met cycle, Glutatione metabolism |
| Hydroxyproline | Urea Cycle |
| Hypoxanthine | Purine Metabolism |
| Isoleucine (Ile) | BCAA Metabolism |
| Inosine monophosphate (IMP) | Purine Metabolism |
| Inosine | Purine Metabolism |
| Isocitric acid | Citric acid cycle |
| Lactic acid | Glycolysis |
| Leucine (Leu) | BCAA Metabolism |
| Lysine (Lys) | Lysine Metabolism |
| Malic acid | Citric acid cycle |
| Malonyl CoA | Citric acid cycle, Lipid Metabolism |
| Methionine (Met) | Methionine Cycle, Methylation, Transsulfuration pathway |
| Mevalonic acid | Lipid Metabolism |
| N,N-Dimethylglycine | Choline Metabolism |
| N-Acetylglutamic acid | Urea Cycle |
| Nicotinamide Adenine dinucleotide (NAD+) | Nicotinamides |
| Nicotinamide Adenine dinucleotide (NADH) | Nicotinamides |
| Nicotinamide adenine dinucleotide phosphate (NADP+) | Nicotinamides |
| Nicotinamide adenine dinucleotide phosphate (NADPH) | Nicotinamides |
| N-Carbamoylaspartic acid | Urea Cycle |
| Ornithine | Urea Cycle |
| Phenylalanine (Phe) | Polyamines & Creatine |
| Phosphocreatine | Polyamines & Creatine |
| Phosphoenolpyruvic acid | Glycolysis |
| Proline (Pro) | Urea Cycle |
| Phosphoribosyl pyrophosphate (PRPP) | Pentose Phosphate Pathway |
| Putrescine | Polyamines & Creatine, Urea Cycle |
| Pyruvic acid | Glycolysis |
| Ribose 1-phosphate | Pentose Phosphate Pathway |
| Ribose 5-phosphate | Pentose Phosphate Pathway |
| Ribulose 5-phosphate | Pentose Phosphate Pathway |
| S-Adenosylhomocysteine | Methionine Cycle |
| S-Adenosylmethionine | Methionine Cycle |
| Sarcosine | Choline Metabolism |
| Sedoheptulose 7-phosphate | Pentose Phosphate Pathway |
| Serine (Ser) | Lipid Metabolism |
| Spermidine | Polyamines & Creatine |
| Spermine | Polyamines & Creatine |
| Succinic acid | Citric acid cycle |
| Threonine (Thr) | Lipid Metabolism |
| Tryptophan (Trp) | Trp Metabolism |
| Tyrosine (Tyr) | Polyamines & Creatine |
| UDP-glucose | Pentose Phosphate Pathway |
| Urea | Urea Cycle |
| Uric acid | Purine Metabolism |
| Valine (Val) | BCAA Metabolism |
| Xanthine | Purine Metabolism |
| Xanthosine monophosphate (XMP) | Purine Metabolism |
| Xylulose 5-phosphate | Pentose Phosphate Pathway |
| β-Alanine (β-Ala) | Glycolysis |
| γ-Aminobutyric acid (GABA) | Polyamines & Creatine |

TABLE 3

Metabolomics data of human CSF samples

| Compound name | Concentration (μM) | | | | | | Comparative Analysis | |
|---|---|---|---|---|---|---|---|---|
| | Control (N = 40) | | | BD (N = 54) | | | | |
| | Mean | S.D. | N | Mean | S.D. | N | P-value ‖ | |
| Nicotinamide Adenine dinucleotide (NAD+) | 0.7 | 0.01 | 7 | 0.7 | 0.04 | 12 | 0.176 | |
| cyclic AMP (cAMP) | 0.03 | 7.23E−03 | 39 | 0.03 | 8.13E−03 | 54 | 0.533 | |
| cyclic GMP (cGMP) | 7.15E−03 | 2.99E−03 | 34 | 7.54E−03 | 3.35E−03 | 44 | 0.594 | |
| Xanthine | 2.0 | 0.4 | 40 | 2.1 | 0.6 | 54 | 0.377 | |
| Nicotinamide Adenine dinucleotide (NADH) | 0.8 | N.A. | 1 | 0.8 | N.A. | 1 | N.A. | |
| ADP-ribose | 4.41E−03 | 3.09E−04 | 10 | 4.81E−03 | 8.27E−04 | 11 | 0.154 | |
| Mevalonic acid | N.D. | N.A. | 0 | 0.03 | N.A. | 1 | N.A. | |
| UDP-glucose | 9.43E−03 | N.A. | 1 | N.D. | N.A. | 0 | N.A. | |
| Uric acid | 23 | 8.9 | 40 | 29 | 11 | 54 | 0.008 | ** |
| Nicotinamide adenine dinucleotide phosphate (NADP+) | 0.02 | 3.33E−03 | 11 | 0.02 | 2.24E−03 | 14 | 0.978 | |
| Fructose 6-phosphate | 0.1 | 0.03 | 28 | 0.1 | 0.02 | 37 | 0.049 | * |
| Acetoacetyl CoA | 6.26E−03 | 8.17E−04 | 3 | 7.14E−03 | 7.55E−04 | 5 | 0.173 | |
| Acetyl CoA | 0.01 | 3.14E−03 | 15 | 0.01 | 2.07E−03 | 13 | 0.996 | |
| Folio acid | 0.01 | 4.40E−04 | 4 | 0.01 | 1.38E−03 | 11 | 0.426 | |
| Ribose 5-phosphate | 0.03 | 7.95E−03 | 11 | 0.04 | 0.02 | 23 | 0.013 | * |
| CoA | 0.2 | 6.06E−03 | 5 | 0.2 | 9.18E−03 | 5 | 0.037 | * |
| Erythrose 4-phosphate | 0.3 | N.A. | 1 | 0.3 | 0.07 | 6 | N.A. | |
| Glyceraldehyde 3-phosphate | 0.1 | 0.06 | 3 | 0.2 | 0.02 | 3 | 0.629 | |
| Nicotinamide adenine dinucleotide phosphate (NADPH) | 0.4 | 0.02 | 8 | 0.5 | 0.03 | 13 | 0.104 | |
| Glycerol 3-phosphate | 3.7 | 1.1 | 40 | 3.8 | 1.2 | 54 | 0.619 | |
| Malonyl CoA | 0.02 | 6.14E−04 | 6 | 0.02 | 1.41E−03 | 8 | 0.195 | |
| Phosphocreatine | 0.9 | 0.3 | 40 | 1.0 | 0.4 | 54 | 0.135 | |
| Xanthosine monophosphate (XMP) | 0.02 | 1.38E−03 | 10 | 0.03 | 2.78E−03 | 11 | 0.210 | |
| N-Acetylglutamic acid | N.D. | N.A. | 0 | 0.3 | 0.2 | 8 | N.A. | |
| Adenylosuccinic acid | 0.03 | 2.32E−03 | 11 | 0.03 | 2.85E−03 | 15 | 0.927 | |
| Fructose 1,6-diphosphate | 0.05 | 6.06E−03 | 4 | 0.06 | 0.01 | 5 | 0.377 | |
| N-Carbamoylaspartic acid | 0.02 | 4.64E−03 | 6 | 0.03 | 7.05E−03 | 6 | 0.092 | |
| Phosphoribosyl pyrophosphate (PRPP) | 0.03 | 9.45E−04 | 2 | 0.03 | 3.59E−04 | 2 | 0.176 | |
| 2-Phosphoglyceric acid | 0.04 | N.A. | 1 | 5.05E−03 | N.A. | 1 | N.A. | |
| 3-Phosphoglyceric acid | 0.02 | 0.01 | 3 | 0.03 | 0.03 | 8 | 0.527 | |
| Phosphoenolpyruvic acid | 0.03 | 0.03 | 5 | 0.07 | 0.04 | 10 | 0.143 | |
| 2-Oxoisovaleric acid | 3.6 | 0.5 | 40 | 3.9 | 0.6 | 54 | 0.021 | * |
| Lactic acid | 1,480 | 171 | 40 | 1,601 | 247 | 54 | 0.006 | ** |
| Adenosine diphosphate (ADP) | 0.5 | 0.04 | 2 | 0.5 | 0.02 | 6 | 0.907 | |
| Guanosine triphosphate (GTP) | 0.7 | 0.04 | 4 | 0.7 | 0.05 | 12 | 0.469 | |
| Adenosine triphosphate (ATP) | N.D. | N.A. | 0 | 1.0 | 0.06 | 7 | N.A. | |
| Glycolic acid | 8.1 | 2.8 | 40 | 8.4 | 2.2 | 52 | 0.467 | |
| Pyruvic acid | 15 | 6.9 | 40 | 21 | 11 | 54 | 0.002 | ** |
| 2-Hydroxyglutaric acid | 0.03 | 0.02 | 3 | 0.09 | 0.06 | 6 | 0.144 | |
| Carbamoylphosphate | 0.4 | 0.4 | 4 | 1.3 | 1.0 | 5 | 0.127 | |
| Succinic acid | 3.6 | 1.4 | 38 | 4.0 | 1.3 | 53 | 0.255 | |
| Citric acid | 180 | 35 | 40 | 227 | 54 | 54 | <.0001 | *** |
| Isocitric acid | 3.4 | 0.9 | 40 | 4.8 | 1.1 | 54 | <.0001 | *** |
| cis-Aconitic acid | 1.2 | 0.4 | 40 | 1.7 | 0.5 | 54 | <.0001 | *** |
| Urea | 5,035 | 999 | 40 | 4,392 | 968 | 54 | 0.002 | ** |
| Glycine (Gly) | 4.4 | 1.7 | 40 | 4.9 | 2.9 | 54 | 0.323 | |
| Alanin (Ala) | 32 | 9.8 | 40 | 37 | 10 | 54 | 0.033 | * |
| γ-Aminobutyric acid (GABA) | 0.5 | 0.2 | 13 | 0.5 | 0.09 | 13 | 0.357 | |
| Serine (Ser) | 31 | 4.6 | 40 | 30 | 6.9 | 54 | 0.663 | |
| Creatinine | 66 | 12 | 40 | 67 | 11 | 54 | 0.590 | |
| Valine (Val) | 22 | 7.7 | 40 | 23 | 7.5 | 54 | 0.698 | |
| Threonine (Thr) | 32 | 7.6 | 40 | 32 | 7.9 | 54 | 0.998 | |
| Hydroxyproline | 1.9 | 0.3 | 40 | 2.0 | 0.4 | 54 | 0.086 | |
| Creatine | 57 | 8.1 | 40 | 58 | 8.2 | 54 | 0.567 | |
| Leucine (Leu) | 16 | 3.9 | 40 | 17 | 4.6 | 54 | 0.267 | |
| Isoleucine (Ile) | 4.6 | 1.5 | 40 | 5.3 | 2.1 | 54 | 0.098 | |
| Asparagine (Asn) | 6.9 | 1.3 | 40 | 7.0 | 1.1 | 54 | 0.555 | |
| Ornithine | 5.2 | 1.0 | 40 | 5.6 | 1.9 | 54 | 0.173 | |

TABLE 3-continued

Metabolomics data of human CSF samples

| Compound name | Concentration (μM) | | | | | | Comparative Analysis |
| --- | --- | --- | --- | --- | --- | --- | --- |
| | Control (N = 40) | | | BD (N = 54) | | | |
| | Mean | S.D. | N | Mean | S.D. | N | P-value [||] |
| Asparagic acid (Asp) | N.D. | N.A. | 0 | 11 | N.A. | 1 | N.A. |
| Hypoxanthine | 2.9 | 0.5 | 40 | 3.1 | 0.6 | 54 | 0.146 |
| Glutamine (Gln) | 692 | 67 | 40 | 711 | 66 | 54 | 0.171 |
| Lysine (Lys) | 36 | 6.6 | 40 | 36 | 7.0 | 54 | 0.774 |
| Glutamic acid (Glu) | N.D. | N.A. | 0 | 2.9 | N.A. | 1 | N.A. |
| Methionine (Met) | 4.0 | 1.0 | 40 | 4.0 | 1.0 | 54 | 0.698 |
| Histidine (His) | 12 | 1.5 | 40 | 12 | 1.5 | 54 | 0.494 |
| Phenylalanine (Phe) | 9.6 | 1.5 | 40 | 10 | 1.7 | 54 | 0.165 |
| Arginine (Arg) | 20 | 3.2 | 40 | 20 | 3.3 | 54 | 0.455 |
| Citrulline | 2.2 | 0.4 | 40 | 2.3 | 0.5 | 54 | 0.150 |
| Tyrosine (Tyr) | 9.7 | 2.3 | 40 | 11 | 2.4 | 54 | 0.084 |
| Tryptophan (Trp) | 1.8 | 0.3 | 40 | 2.0 | 0.3 | 54 | 0.035 * |
| Inosine | N.D. | N.A. | 0 | 1.2 | NA | 1 | N.A. |
| Argininosuccinic acid | 0.8 | 0.05 | 2 | 0.8 | 0.07 | 3 | 0.962 |

N.D.: Not Detected.
N.A.: Not Available.
[||] Unpaired t-test.
* P < 0.05,
** P < 0.01,
*** P < 0.001

The volume (50 μL) of CSF sample was added to 450 μL it methanol containing internal standards, and mixed. Then, 450 μL chloroform and 200 μL Milli-Q water was added to the mixture. After mixture, the mixture was centrifuged at 2,300×g and 4° C. for 5 min. Subsequently, 800 μL of upper aqueous layer was centrifugally filtered through a Millipore 5-kDa cutoff filter at 9,100×g and 4° C. for 120 min to remove proteins. The filtrate was centrifugally concentrated and re-suspended in 25 μL of Milli-Q water for analysis.

Cationic compounds were measured in the positive mode of CE-TOFMS (Agilent CE-TOFMS system Machine No. 3, Fused silica capillary, i.d. 50 μM×80 cm), and anionic compounds were measured in the positive and negative modes of CE-MS/MS (Agilent CE system and Agilent 6400 TripleQuad LC/MS Machine No. QqQ01, Fused silica capillary, i.d. 50 μM×80 cm), as reported previously (Soga et al., Anal. Chem. 2000; 72(6):1236-1241; Soga et al., Anal Chem. 2002; 74(10):2233-2239; Soga et al., J. Proteome Res. 2003; 2(5):488-494, which are incorporated in their entireties by reference herein). Peaks detected by CE-TOFMS and CE-MS/MS were extracted using automatic integration software (MasterHands, Keio University, Tsuruoka, Japan) (Sugimoto et al., Metabolomics. 2009; 6(1):78-95, which is incorporated in its entirety by reference herein) and MassHunter Quantitative Analysis B.04.00, Agilent Technologies, Santa Clara, Calif., USA) in order to obtain peak information including m/z, migration time (MT), and peak area. The peaks were annotated with putative metabolites from the HMT metabolite database based on their MTs in CE and m/z values determined by TOFMS. The tolerance range for the peak annotation was configured at ±0.5 min for MT and ±10 ppm for m/z. In addition, concentrations of metabolites were calculated by normalizing the peak area of each metabolite with respect to the area of the internal standard and by using standard curves, which were obtained by three-point calibrations.

Metabolomics analyses of CSF samples from 40 healthy controls and 54 BD patients were thus performed. There were no differences between healthy controls and BD patients for age and BMI (Table 1). Table 1 shows demographics and clinical characteristics of the BD patients. 116 major metabolic substances were measured in various pathways, of which 72 were detected in CSF, and the remaining 44 were under the detection limit (Tables 2 and 3). To select the substances showing significant differences between healthy controls and BD patients, both unpaired t-tests and Wilcoxon rank sum tests were first performed between healthy controls and BD patients. Thirteen compounds, including uric acid, fructose 6-phosphate, ribose 5-phosphate, CoA, 2-oxoisovaleric acid, lactic acid (lactate), pyruvic acid (pyruvate), citric acid (citrate), isocitric acid (isocitrate), cis-aconitic acid (cis-aconitate), urea, alanine, and tryptophan, were significantly altered (Table 4). Pyruvate, citrate, isocitrate, cis-aconitate, are molecules in the citric acid cycle (also known as the Krebs cycle) (FIG. 1).

TABLE 4

Analysis of Maximum Likelihood Estimates in variate logistic regression model

| Parameter | DF | Estimate | Standard Error | Wald Chi-Square | Pr > ChiSq |
|---|---|---|---|---|---|
| Intercept | 1 | −3.962 | 204.7 | 0.0004 | 0.9846 |
| BMI | 1 | 0.167 | 0.1597 | 1.0927 | 0.2959 |
| Uric acid | 1 | 0.0163 | 0.0101 | 2.6018 | 0.1067 |
| CoA | 1 | 1.9836 | 5.892 | 0.1133 | 0.7364 |
| Glycerol 3-phosphate | 1 | 198.4 | 6209.7 | 0.001 | 0.9745 |
| Pyruvic acid | 1 | −0.065 | 0.0343 | 3.5574 | 0.0593 |
| N-Acetylglutamic acid | 1 | 54.094 | 19.9823 | 7.3285 | 0.0068 |
| 2-Hydroxyglutaric acid | 1 | −1.448 | 1.8945 | 0.5841 | 0.4447 |
| 2-Oxoglutaric acid | 1 | 0.7366 | 0.3172 | 5.3936 | 0.0202 |
| Citric acid | 1 | −0.021 | 0.0613 | 0.1177 | 0.7315 |
| cis-Aconitic acid | 1 | −0.906 | 4.7594 | 0.0362 | 0.849 |
| Isocitric acid | 1 | −0.37 | 0.9864 | 0.1408 | 0.7075 |
| Urea | 1 | 0.0004 | 0.0005 | 0.5337 | 0.4651 |
| β-Alanine (β-Ala) | 1 | −1.594 | 0.6387 | 6.2257 | 0.0126 |
| Serine (Ser) | 1 | −0.06 | 0.0234 | 6.4833 | 0.0109 |
| Valine (Val) | 1 | −0.011 | 0.0118 | 0.8958 | 0.3439 |
| Threonine (Thr) | 1 | −0.026 | 0.022 | 1.3574 | 0.244 |
| Ornithine | 1 | 0.0198 | 0.0316 | 0.3939 | 0.5302 |
| Glutamine (Gln) | 1 | −0.039 | 0.034 | 1.3134 | 0.2518 |
| Arginine (Arg) | 1 | 0.0429 | 0.0218 | 3.8767 | 0.049 |

Multivariate logistic regression analysis was performed to evaluate the association between the 13 metabolites and BD. A stepwise selection-elimination method was used, and the significance level was set at 5%. At least one parameter, isocitrate, was independently associated with BD. After cross-validation testing using the jack-knife procedure, the model's sensitivity was 79.6% and specificity was 72.5%. The Hosmer-Lemeshow goodness-of-fit statistic (the internal validation of the logistic regression model) was 12.1450 with 8 DF (P=0.1449), indicating a good fit of the model (Table 5).

TABLE 5

Independent predictor in CSF samples of BD patients by logistic regression

| Parameter | Odds ratio (95% confidence interval) | P value |
|---|---|---|
| Isocitrate | 4.402 (2.249-7.266) | <0.0001 |

Logistic function, P = {1 + exp (5.3463 − 1.3967X)}
P: Probability of being statistically-discriminated as BD,
X: Isocitrate To investigate whether isocitrate is affected by clinical data or medication in BD patients, additional multiple regression analyses were performed. Because isocitrate was significantly (P<0.0001) altered in the CSF from BD patients after logistic regression, isocitrate was focused on for subsequent analyses. The major finding of this study was that CSF levels of isocitrate in BD patients were significantly higher than those in healthy controls, which was unrelated to medication. This is believed to be the first study showing increased CSF levels of isocitrate in BD patients.

Example 2

This example demonstrates that the levels of various metabolites in serum can be used to predict a diagnosis of bipolar disorder (BD) in human patients. The study was performed as described in Example 1 unless otherwise noted.

Metabolomics analyses of serum samples from 39 healthy controls and 54 BD patients were performed. There were no differences between healthy controls and BD patients for age and BMI (Table 6). Table 6 shows demographics and clinical characteristics of the BD patients. 116 major metabolic substances were measured in various pathways, of which 82 were detected in serum, and the remaining 34 were under the detection limit (Tables 7 and 8). To select the substances showing significant differences between healthy controls and BD patients, both unpaired t-tests and Wilcoxon rank sum tests were first performed between healthy controls and BD patients. Eighteen compounds, including uric acid, CoA, glycerol 3-phosphate, pyruvic acid (pyruvate), N-acetylglutamic acid, 2-hydroxyglutaric acid, 2-oxoglutaric acid, citric acid (citrate), cis-aconitic acid (cis-aconitate), urea, β-alanine, serine, tryptophan, ornithine, glutamaic acid (glutamate), and arginine, were significantly altered (Table 8).

TABLE 6

Characteristics of the participants

| | Controls | | Bipolar disorder (BD) | |
|---|---|---|---|---|
| Sex (male) | 39[a] | | 54 | |
| | Median | IQR | Median | IQR |
| Age (years) | 36 | 21-74 | 41 | 20-73 |
| BMI | 25.7 | 18.3-32.5 | 24.1 | 19.6-32.5 |
| Diagnosis | | | N | % |
| Bipolar disorder type I (BP I) | | | 31 | 57.4 |
| Bipolar disorder type II (BP II) | | | 17 | 31.5 |
| Not otherwise specified (NOS) | | | 6 | 11.1 |
| Clinical data | | | Median | IQR |
| Age first symptoms | | | 20 | 5-58 |
| Depressive episodes[c] | | | 6 | 0-60 |
| Hypomanic episodes[b] | | | 6 | 0-40 |
| Manic episodes[b] | | | 1 | 0-10 |
| Mixed episodes[b] | | | 0 | 0-25 |
| GAF[b] | | | 70 | 21-90 |
| MADRS[d] | | | 4 | 0-44 |
| YMRS[e] | | | 1 | 0-11 |
| No of episodes[b] | | | 18 | 1-80 |

TABLE 6-continued

Characteristics of the participants

|  | Controls | Bipolar disorder (BD) | |
|---|---|---|---|
|  |  | N | % |
| Psychosis episodes[b] |  | 25 | 46.3 |
| Medication |  |  |  |
| Mood stabilizer |  | 44 | 81.5 |
| Lithium (Li) |  | 34 | 63 |
| Anticonvulsants |  | 19 | 35.2 |
| Valproate (VPA) |  | 7 | 13 |
| Lamotrigine |  | 12 | 22.2 |
| Antidepressants |  | 20 | 37 |
| Anxiolytics |  | 11 | 20.4 |
| Antipsychotics |  | 16 | 29.6 |

[a]Missing data for 1 individual in the control group
[b]Missing data for 1 individual in the patient group
[c]Missing data for 2 individual in the patient group
[d]Missing data for 10 individual in the patient group
[e]Missing data for 11 individual in the patient group
IQR: Interquartile Range
GAF: Global Assessment of Functioning
MADRS: Montgomery-Åsberg Depression Rating Scale
YMRS: Young Mania Rating Scale

TABLE 7

Predictors concentration in serum

| | Concentration (µM) | | | | | | Comparative Analysis | |
|---|---|---|---|---|---|---|---|---|
| | Control | | | BD patients | | | | |
| Compound name | Mean | S.D. | N | Mean | S.D. | N | P Value[∥] | |
| Nicotinamide Adenine dinucleotide (NAD+) | 1.0 | 0.06 | 38 | 1.0 | 0.04 | 51 | 0.703 | |
| cyclic AMP (cAMP) | 0.008 | 0.007 | 38 | 0.007 | 0.004 | 52 | 0.871 | |
| cyclic GMP (cGMP) | 0.013 | 0.014 | 8 | 0.007 | 0.004 | 16 | 0.254 | |
| Xanthine | 3.5 | 1.1 | 39 | 3.8 | 1.2 | 54 | 0.271 | |
| Mevalonic acid | 0.03 | 0.02 | 8 | 0.05 | 0.05 | 18 | 0.063 | |
| UDP-glucose | 0.4 | 0.03 | 24 | 0.4 | 0.014 | 21 | 0.445 | |
| Uric acid* | 339 | 46 | 39 | 368 | 66 | 54 | 0.014 | * |
| IMP | 0.09 | 0.010 | 21 | 0.08 | 0.005 | 26 | 0.401 | |
| Oxidised Nicotinamide Adenine dinucleotide phophate (NADP+) | 0.10 | 0.015 | 11 | 0.10 | 0.004 | 16 | 0.396 | |
| Glucose 6-phosphate | 0.2 | 0.05 | 39 | 0.2 | 0.06 | 53 | 0.321 | |
| Fructose 6-phosphate | 0.05 | 0.02 | 37 | 0.06 | 0.02 | 45 | 0.421 | |
| Ribose 5-phosphate | 0.03 | N.A. | 1 | N.D. | N.A. | 0 | N.A. | |
| Acetoacetyl CoA | 0.04 | 9.7E-04 | 5 | 0.04 | 1.2E-04 | 2 | 0.353 | |
| Acetyl CoA | 0.02 | 0.03 | 3 | 0.002 | 0.003 | 3 | 0.450 | |
| Folic acid | N.D. | N.A. | 0 | 0.03 | 6.0E-04 | 2 | N.A. | |
| CoA | 0.3 | 0.002 | 2 | 0.3 | 0.004 | 5 | 0.049 | * |
| Ribose 1-phosphate | 0.3 | 0.15 | 36 | 0.3 | 0.14 | 51 | 0.899 | |
| Ribulose 5-phosphate | 0.10 | 0.02 | 14 | 0.11 | 0.013 | 16 | 0.302 | |
| Erythrose 4-phosphate | 0.011 | N.A. | 1 | 0.011 | N.A. | 1 | N.A. | |
| Glyceraldehyde 3-phosphate | N.D. | N.A. | 0 | 0.09 | 0.07 | 3 | N.A. | |
| Reduced Nicotinamide Adenine dinucleotide phophate (NADPH) | 0.7 | 0.008 | 2 | 0.7 | 0.02 | 7 | 0.686 | |
| Phosphocreatine | 0.06 | N.A. | 1 | N.D. | N.A. | 0 | N.A. | |
| Adenylosuccinic acid | 0.05 | 0.005 | 8 | 0.05 | 0.002 | 13 | 0.554 | |
| Fructose 1,6-diphosphate | 0.2 | 0.05 | 2 | 0.13 | 0.02 | 3 | 0.598 | |
| 6-Phosphogluconic acid | 0.3 | N.A. | 1 | 0.2 | N.A. | 1 | N.A. | |
| N-Carbamoylaspartic acid | 0.08 | 0.04 | 39 | 0.10 | 0.04 | 54 | 0.170 | |
| PRPP | N.D. | N.A. | 0 | 0.03 | 1.3E-03 | 2 | N.A. | |
| 2-Phosphoglyceric acid | 0.03 | 0.03 | 6 | 0.02 | 0.02 | 9 | 0.958 | |
| 3-Phosphoglyceric acid | 0.2 | 0.08 | 39 | 0.2 | 0.11 | 53 | 0.471 | |
| 2-Oxoisovaleric acid | 14 | 2.5 | 39 | 14 | 2.8 | 54 | 0.507 | |
| GDP | 0.3 | 0.03 | 11 | 0.3 | 0.010 | 18 | 0.860 | |
| Lactic acid | 2,173 | 592 | 39 | 2,061 | 489 | 54 | 0.321 | |
| ADP | 0.6 | 0.05 | 15 | 0.6 | 0.02 | 18 | 0.348 | |
| GTP | 2.3 | 0.005 | 2 | 2.3 | 0.08 | 6 | 0.917 | |
| ATP | 5.0 | 0.15 | 5 | 4.9 | 0.2 | 8 | 0.513 | |
| Glycerol 3-phosphate | 1.8 | 0.5 | 39 | 1.6 | 0.5 | 54 | 0.074 | |
| Glycolic acid | 8.2 | 1.6 | 39 | 8.4 | 1.8 | 51 | 0.554 | |
| Pyruvic acid | 35 | 23 | 39 | 48 | 24 | 54 | 0.009 | ** |
| N-Acetylglutamic acid | 0.2 | 0.03 | 37 | 0.3 | 0.05 | 54 | 0.002 | ** |
| 2-Hydroxyglutaric acid | 0.6 | 0.2 | 39 | 0.7 | 0.3 | 54 | 0.046 | * |
| Succinic acid | 6.2 | 1.0 | 39 | 6.1 | 1.1 | 54 | 0.954 | |
| Malic acid | N.D. | N.A. | 0 | 1.9 | 2.1 | 2 | N.A. | |

TABLE 7-continued

Predictors concentration in serum

| Compound name | Concentration (μM) | | | | | | Comparative Analysis | |
|---|---|---|---|---|---|---|---|---|
| | Control | | | BD patients | | | | |
| | Mean | S.D. | N | Mean | S.D. | N | P Value ‖ | |
| 2-Oxoglutaric acid | 4.0 | 2.2 | 39 | 8.7 | 5.5 | 54 | <.0001 | *** |
| Citric acid | 92 | 21 | 39 | 73 | 20 | 54 | <.0001 | *** |
| cis-Aconitic acid | 1.2 | 0.3 | 39 | 1.0 | 0.3 | 54 | 0.012 | * |
| Isocitric acid | 4.2 | 1.1 | 39 | 3.8 | 1.2 | 54 | 0.057 | |
| Urea | 5,623 | 1,145 | 39 | 4,955 | 1,039 | 54 | 0.004 | ** |
| Glycine (Gly) | 360 | 50 | 39 | 359 | 54 | 54 | 0.947 | |
| Alanin (Ala) | 449 | 79 | 39 | 475 | 76 | 54 | 0.121 | |
| Sarcosine | 1.5 | 1.0 | 38 | 1.4 | 1.0 | 51 | 0.990 | |
| β-Alanine (β-Ala) | 3.7 | 1.2 | 39 | 2.7 | 0.8 | 54 | <.0001 | *** |
| γ-Aminobutyric acid | N.D. | N.A. | 0 | 0.2 | 0.07 | 6 | N.A. | |
| N,N-Dimethylglycine | 3.5 | 1.7 | 39 | 3.5 | 2.0 | 54 | 0.998 | |
| Choline | 13 | 4.2 | 39 | 12 | 3.8 | 54 | 0.366 | |
| Serine (Ser) | 230 | 28 | 39 | 209 | 32 | 54 | 0.002 | ** |
| Creatinine | 84 | 9.7 | 39 | 85 | 13 | 54 | 0.884 | |
| Prorine (Pro) | 268 | 89 | 39 | 278 | 121 | 54 | 0.653 | |
| Valine (Val) | 340 | 40 | 39 | 324 | 45 | 54 | 0.084 | |
| Betaine | 50 | 13 | 39 | 48 | 16 | 54 | 0.526 | |
| Threonine (Thr) | 163 | 24 | 39 | 150 | 27 | 54 | 0.020 | * |
| Hydroxyproline | 16 | 7.3 | 39 | 17 | 8.9 | 54 | 0.562 | |
| Creatine | 31 | 16 | 39 | 34 | 13 | 54 | 0.265 | |
| Isoleucine (Ile) | 82 | 12 | 39 | 83 | 17 | 54 | 0.760 | |
| Leucine (Leu) | 187 | 20 | 39 | 184 | 25 | 54 | 0.424 | |
| Asparagine (Asn) | 55 | 5.7 | 39 | 54 | 7.8 | 54 | 0.252 | |
| Ornithine | 79 | 19 | 39 | 71 | 16 | 54 | 0.019 | * |
| Asparagic acid (Asp) | 37 | 7.5 | 39 | 36 | 7.9 | 54 | 0.690 | |
| Hypoxanthine | 10 | 3.0 | 39 | 10 | 2.8 | 54 | 0.966 | |
| Glutamine (Gln) | 723 | 63 | 39 | 701 | 98 | 54 | 0.194 | |
| Lysine (Lys) | 225 | 33 | 39 | 223 | 31 | 54 | 0.729 | |
| Glutamic acid (Glu) | 103 | 27 | 39 | 122 | 40 | 54 | 0.006 | ** |
| Methionine (Met) | 24 | 3.0 | 39 | 23 | 3.8 | 54 | 0.593 | |
| Histidine (His) | 97 | 10 | 39 | 95 | 11 | 54 | 0.301 | |
| Carnitine | 59 | 12 | 39 | 62 | 10 | 54 | 0.237 | |
| Phenylalanine (Phe) | 87 | 10 | 39 | 87 | 13 | 54 | 0.990 | |
| Arginine (Arg) | 122 | 19 | 39 | 131 | 23 | 54 | 0.039 | * |
| Citrulline | 37 | 6.4 | 39 | 38 | 7.1 | 54 | 0.738 | |
| Thyosine (Tyr) | 65 | 12 | 39 | 68 | 17 | 54 | 0.239 | |
| Triptophane (Trp) | 72 | 9.3 | 39 | 71 | 14 | 54 | 0.737 | |
| Cystathionine | 1.1 | 0.2 | 3 | 0.8 | 0.13 | 2 | 0.216 | |
| Inosine | 3.2 | 1.2 | 11 | 4.5 | 2.2 | 13 | 0.087 | |
| Guanosine | N.D. | N.A. | 0 | 1.4 | 0.3 | 5 | N.A. | |

N.D.: Not Detected.
N.A.: Not Available.
‖ one way ANOVA
(* <0.05,
** <0.01,
*** <0.001)

TABLE 8

Analysis of Maximum Likelihood Estimates in variate logistic regression model

| Parameter | DF | Estimate | Standard Error | Wald Chi-Square | Pr > ChiSq |
|---|---|---|---|---|---|
| Intercept | 1 | −3.962 | 204.7 | 0.0004 | 0.9846 |
| BMI | 1 | 0.167 | 0.1597 | 1.0927 | 0.2959 |
| Uric acid | 1 | 0.0163 | 0.0101 | 2.6018 | 0.1067 |
| CoA | 1 | 1.9836 | 5.892 | 0.1133 | 0.7364 |
| Glycerol 3-phosphate | 1 | 198.4 | 6209.7 | 0.001 | 0.9745 |
| Pyruvic acid | 1 | −0.065 | 0.0343 | 3.5574 | 0.0593 |
| N-Acetylglutamic acid | 1 | 54.094 | 19.9823 | 7.3285 | 0.0068 |
| 2-Hydroxyglutaric acid | 1 | −1.448 | 1.8945 | 0.5841 | 0.4447 |
| 2-Oxoglutaric acid | 1 | 0.7366 | 0.3172 | 5.3936 | 0.0202 |
| Citric acid | 1 | −0.021 | 0.0613 | 0.1177 | 0.7315 |
| cis-Aconitic acid | 1 | −0.906 | 4.7594 | 0.0362 | 0.849 |
| Isocitric acid | 1 | −0.37 | 0.9864 | 0.1408 | 0.7075 |
| Urea | 1 | 0.0004 | 0.0005 | 0.5337 | 0.4651 |
| β-Alanine (β-Ala) | 1 | −1.594 | 0.6387 | 6.2257 | 0.0126 |
| Serine (Ser) | 1 | −0.06 | 0.0234 | 6.4833 | 0.0109 |
| Valine (Val) | 1 | −0.011 | 0.0118 | 0.8958 | 0.3439 |
| Threonine (Thr) | 1 | −0.026 | 0.022 | 1.3574 | 0.244 |
| Ornithine | 1 | 0.0198 | 0.0316 | 0.3939 | 0.5302 |
| Glutamine (Gln) | 1 | −0.039 | 0.034 | 1.3134 | 0.2518 |
| Arginine (Arg) | 1 | 0.0429 | 0.0218 | 3.8767 | 0.049 |

Multivariate logistic regression analysis was performed to evaluate the association between the 18 metabolites and BD. A stepwise selection-elimination method was used, and the significance level was set at 5%. At least six compounds, pyruvic acid, N-acetylglutamic acid, 2-oxoglutaric acid, β-alanine, serine, and arginine, were independently associated with BD (Table 9). After cross-validation testing using the jack-knife procedure, the model's sensitivity was 85.2% and specificity was 76.9%. The Hosmer-Lemeshow goodness-of-fit statistic (the internal validation of the logistic regression model) was 3.6123 with 8 DF (P=0.8903), indicating a good fit of the model.

TABLE 9

Independent predictor in serum samples of BD patients by logistic regression

| Parameter | Odds ratio (95% confidence interval) | P value |
|---|---|---|
| Pyruvic acid | 0.940 (0.896-0.987) | 0.0128 |
| N-Acetylglutamic acid | >999.999 (>999.999->999.999) | 0.0042 |
| 2-Oxoglutaric acid | 1.683 (1.218-2.324) | 0.0016 |
| β-Alanine | 0.264 (0.109-0.638) | 0.0031 |
| Serine | 0.947 (0.918-0.977) | 0.0007 |
| Arginine | 1.045 (1.009-1.082) | 0.0149 |

Logistic function, $P = 1/\{1 + \exp(-1.0826 + 0.0614X_1 - 40.1927X_2 - 0.5203X_3 + 1.3329X_4 + 0.0544X_5 - 0.0436X_6)\}$.
P: Probability of being statistically-discriminated as BD
$X_1$, Pyruvic acid; $X_2$, N-Acetylglutamic acid; $X_3$, 2-Oxoglutaric acid; $X_4$, β-Alanine; $X_5$, Serine; $X_6$, Arginine Example 3

This example demonstrates that the levels of various metabolites in both cerebrospinal fluid (CSF) and serum can be used to predict a diagnosis of bipolar disorder (BD) in human patients. For example, levels of isocitrate were found to positively correlate with BD. This example is based on the results from Examples 1 and 2.

Evaluation of combinatorial use of markers in CSF and serum samples: Multivariate logistic regression analysis was performed to evaluate the association between the metabolites and BD. A stepwise selection-elimination method was used, and the significance level was set at 5%. At least five compounds, isocitric acid (isocitrate; CSF), cis-aconitic acid (CSF), uric acid (serum), citric acid (serum), and serine (serum), was independently associated with BD (Table 10). After cross-validation testing using the jack-knife procedure, the model's sensitivity was 88.89% and specificity was 82.50%. The Hosmer-Lemeshow goodness-of-fit statistic (the internal validation of the logistic regression model) was 13.7635 with 8 DF (P=0.0881), indicating a good fit of the model.

TABLE 10

Independent predictors in CSF and serum samples of bipolar disorder by multivariable logistic regression

| Parameter | Odds ratio (95% confidence interval) | P value |
|---|---|---|
| Isocitric acid (CSF) | 5.845 (2.140-15.964) | 0.0006 |
| cis-Aconitic acid (CSF) | 16.647 (1.594-173.805) | 0.0188 |
| Uric acid (serum) | 1.015 (1.000-1.030) | 0.0445 |
| Citric acid (serum) | 0.932 (0.893-0.972) | 0.0011 |
| Serine (serum) | 0.955 (0.927-0.984) | 0.0028 |

Logistic function, $P = 1/\{1 + \exp(-0.93536 - 0.15478X_1 - 0.13133X_2 - 0.00063945X_3 + 0.00717X_4 + 0.00393X_5)\}$.
$X_1$, Isocitric acid; $X_2$, cis-Aconitic acid; $X_3$, Uric acid; $X_4$, Citric acid; $X_5$, Serine Example 4

This example demonstrates that substrates, products, and/or enzymes of isocitrate metabolism can be used as biomarkers and/or for screening. This example also demonstrates that subunits of isocitrate dehydrogenase 3 (IDH3) can be used as therapeutic targets, as well as biomarker and screening tools.

ACO1 and ACO2 are localized in the cytosol and the mitochondrial matrix, respectively. ACO1 interconverts citrate and isocitrate in the cytosol, allowing the cell to balance the amount of NADPH generated from isocitrate by IDH1. ACO2 is an enzyme that catalyzes citrate to isocitrate via cis-aconitate in the citric acid cycle. IDH1 is localized in the cytosol, and IDH2 and IDH3 are found in the mitochondrial matrix. The IDH1 and IDH2 enzymes catalyze a redox reaction that converts isocitrate to α-ketoglutarate [also known as 2-oxoglutarate (2-OG)], while reducing NADP to NADPH and liberating $CO_2$. The mitochondrial IDH3 enzyme is an essential element of the citric acid cycle, catalyzing the oxidation of isocitrate to α-ketoglutarate with the reduction of NAD to NADH. The electron transfer chain (ETC) in the mitochondrial membrane is a series of complexes, I-V, that transfer electrons from electron donors to electron acceptors via redox reactions.

Expression of IDH and ACO genes in the dorsolateral prefrontal cortex was investigated. Postmortem brain samples from Brodmann's area 46 were obtained from the Stanley Medical Research Institute (consistent with the description in Kim et al., Schizophr Bull. 2009; 35(6): 1031-1033; and Kim et al., Neuropsychopharmacology. 2010; 35(2):473-482, which are incorporated in their entireties by reference herein). Brain samples were taken from 35 BD patients (17 males, 18 females; mean±SD age, 45.3±10.5 years; PMI, 37.9±18.3 h; brain pH, 6.4±0.3), and 35 controls (26 males, 9 females; mean±SD age, 44.2±7.6 years; PMI, 29.4±12.9 h; brain pH, 6.6±0.3). Diagnoses were made in accordance with DSM-IV criteria. There were no significant demographic differences between the bipolar disorder and control groups, in terms of age, PMI, and sample pH. All BD patients had previously received therapeutic drugs to treat their disease.

Real-time quantitative RT-PCR analysis was conducted using an ABI7900HT Fast Real-Time PCR System (Applied Biosystems, Foster City, Calif.) in both human and rat samples. TaqMan probes and primers for the seven genes (ACO1, ACO2, IDH1, IDH2, IDH3A, IDH3B, IDH3G) and GAPDH (an internal control) (Table 11) were TAQMAN® Gene Expression Assays products (Applied Biosystems). All real-time quantitative RT-PCR reactions were performed in triplicate, based on the standard curve method (consistent with that described in Yamada et al., Hum Genet. 2012; 131(3):443-451, which is incorporated in its entirety by reference herein).

TABLE 11

Informations of IDH and ACO genes for RT-PCR analysis
<Human postmortem brain samples>

| Gene Symbol | Assay ID | RefSeq | Gene Name |
|---|---|---|---|
| GAPDH | Hs02758991_g1 | NM_001256799.1, NM_002046.4 | glyceraldehyde-3-phosphate dehydrogenase |
| IDH1 | Hs01855675_s1 | NM_005896.2 | isocitrate dehydrogenase 1 (NADP+), soluble |
| IDH2 | Hs00158033_m1 | NM_002168.2 | isocitrate dehydrogenase 2 (NADP+), mitochondrial |
| IDH3A | Hs01051668_m1 | NM_005530.2 | isocitrate dehydrogenase 3 (NAD+) alpha |
| IDH3B | Hs00199382_m1 | NM_001258384.1, NM_006899.3, NM_174855.2 | isocitrate dehydrogenase 3 (NAD+) beta |
| IDH3G | Hs00188065_m1 | NM_004135.3, NM_174869.2 | isocitrate dehydrogenase 3 (NAD+) gamma |
| ACO1 | Hs00158095_m1 | NM_001278352.1, NM_002197.2 | aconitase 1, soluble |
| ACO2 | Hs00426616_g1 | NM_001098.2 | aconitase 2, mitochondrial |

Isocitrate is synthesized from citrate via cis-aconitate by the enzyme aconitase (ACO: aconitate hydrotase) (FIG. 1). Two isozymes of aconitase are present in mammalian cells: the mitochondrial enzyme (m-aconitase: ACO2) that functions in the citric acid cycle, and the bifunctional cytosolic enzyme (c-aconitase/IRP1: ACO1) which also plays a role in the regulation of iron metabolism. Isocitrate dehydrogenase (IDH) catalyzes the oxidative decarboxylation of isocitrate, producing α-ketoglutarate (also known as 2-oxoglutarate) and $CO_2$ (FIG. 1). In humans, IDH exists in three forms. The two isoforms, which are mutated in cancer, IDH1 and IDH2, utilize this catalytic process in additional contexts including metabolism and glucose sensing (IDH1) and regulation of oxidative respiration (IDH2). IDH3 primary functions as the allosterically regulated, rate-limiting enzymatic step in the citric acid cycle, while converting NAD+ to NADH in the mitochondria. IDH3 is a heterotetramer with two α-subunits (IDH3A), one β-subunit (IDH3B), and one y-subunit (IDH3G) (FIG. 1).

mRNA levels of ACO and IDH genes in the dorsolateral prefrontal cortex from BD patients (N=35) and controls (N=35) were studied. The mRNA levels of ACO1 (P=0.5008) and ACO2 (P=0.6454) in the dorsolateral prefrontal cortex from BD patients were not different from those of controls. The mRNA levels of IDH3A (P=0.0017) and IDH3B (P=0.0208) in the BD group were significantly lower than that of control group (Table 12). In contrast, mRNA levels of IDH3G (P=0.2287), IDH1 (P=0.7302), and IDH2 (P=0.2858) were not different between the two groups (Table 12).

TABLE 12

Gene expression of ACO and IDH genes in the dorsolateral prefrontal cortex from controls and BD patients

| Genes | Controls (N = 35) | BD Patients (N = 35) | P Value |
|---|---|---|---|
| ACO1 | 1.0681 ± 0.1872 | 1.1196 ± 0.2420 | 0.5008 |
| ACO2 | 0.9116 ± 0.1397 | 0.8970 ± 0.1418 | 0.6454 |
| IDH1 | 1.1790 ± 0.2965 | 1.2096 ± 0.3068 | 0.7302 |
| IDH2 | 1.2332 ± 0.4421 | 1.0961 ± 0.3326 | 0.2858 |
| IDH3A | 1.2082 ± 0.4519 | 0.8966 ± 0.2537 | 0.0017** |
| IDH3B | 1.1040 ± 0.3009 | 0.9362 ± 0.2637 | 0.0208* |
| IDH3G | 1.0666 ± 0.1437 | 1.0286 ± 0.1384 | 0.2287 |

The data are the mean ± S.D.
*$P < 0.05$, **$P < 0.01$ (Mann-Whitney U-test).

Additionally, mRNA levels of IDH3A and IDH3B genes in the dorsolateral prefrontal cortex from BD patients were significantly lower than those of control samples.

The IDH3 enzyme, localized in the mitochondria, plays a central role in the regulation of the citric acid cycle to produce the NADH used for oxidative phosphorylation (FIG. 1). In the citric acid cycle, NAD-dependent IDH3 catalyzes the conversion of isocitrate to α-ketoglutarate, an essential reaction of the cycle that simultaneously changes NAD+ to NADH. The NADH produced in this step and other steps of the citric acid cycle is used to generate adenosine triphosphate (ATP), a molecule universally used in cells as an energy source. Mitochondrial oxidative phosphorylation is also the major ATP-producing pathway, which can supply more than 95% of the total energy requirement in the cells.

The present studies surprisingly found decreased mRNA levels of IDH3A and IDH3B in the dorsolateral prefrontal cortex of BD. The results indicate that a decreased activity of IDH3A and IDH3B in the brain can play a crucial role in the pathogenesis of BD. Based on the central role of IDH3 in the citric acid cycle (FIG. 1), these examples demonstrate an abnormality in the mitochondrial function in BD. These results provide evidence for abnormality in the metabolism of isocitrate by IDH3A and IDH3B in the pathogenesis of BD. Therefore, mitochondrial IDH3 in the citric acid cycle is demonstrated as being a therapeutic target for BD.

Example 5

Genetic association analyses of IDH and ACO genes in BD patients and controls were performed. This example demonstrates that substrates, products, and/or enzymes of isocitrate metabolism can be used as biomarkers and/or screening tools independent of any particular single nucleotide polymorphism (SNP) in a relevant metabolic gene.

BD subjects were collected through three channels. The BD cases (N=1416) were identified using the Swedish National Quality Assurance Registry for Bipolar Disorder (BipoläR) (consistent with the description in Karanti et al., J. Affect. Disord. 2014; 174:303-309; and Sellgren et al., Acta Psychiatr. Scand. 2011; 124(6):447-453, which are incorporated in their entireties by reference herein) Additional subjects were recruited from the Bipolar outpatient clinic at the Northern Stockholm Psychiatry Clinic, Sweden, following physician's referral for BD (N=315). The diagnostic instrument used was a Swedish adaptation of the Affective Disorder Evaluation (consistent with the description in Ryden et al., Acta Psychiatr Scand. 2009; 120(3): 239-246, which is incorporated in its entirety by reference herein), which includes the affective module of the SCID. A further 576 BD cases were recruited from the Stockholm County catchment area, and diagnoses were made according to the DSM-IV criteria. Control subjects, also selected through registers, were group-matched by age, sex and county of residence, and had not been hospitalized with a psychiatric diagnosis. All subjects were at least 18 years old and gave written informed consent to participate. The study was also approved by the Ethical Committee at Karolinska Institute.

Blood samples were obtained and DNA extracted from whole blood using standard methods at Karolinska Institute. Samples were genotyped using one of two arrays: Illumina OmniExpress for Sample 1 (Illumina, Inc. San Diego, Calif., USA) or Affymetrix 6.0 for Sample 2 (Affymetrix, Santa Clara, Calif., USA). All genotyping was conducted at the Broad Institute of Harvard and MIT, and genotypes were called using the Birdsuite algorithm (consistent with the description in Korn et al., Nat Genet. 2008; 40(10):1253-1260, which is incorporated in its entirety by reference herein). The quality control exclusionary measures for subjects were: genotype call rates <95%; ancestry outliers via multidimensional scaling; a randomly selected member of any pair of subjects with high relatedness (pi-hat>0.20); and suspected sample error or contamination. SNPs were excluded for marked departure from Hardy-Weinberg equilibrium (P <$1\times10^{-6}$), low minor allele frequencies (<1%), and non-random genotyping failure, inferred from the flanking haplotype background using the PLINK 'mishap' test (P<$1\times10^{-10}$). Plate-based associations of P<$1\times10^{-6}$ were taken as evidence of non-random plate failure, based on a comparison of allele frequency of each plate to all others and were removed on a plate-by-plate basis. Following quality control steps, Sample 1 consisted of 1415 cases and 1271 controls, and Sample 2 contained 836 cases and 2093 controls.

Genotypes were inputted against autosomal genotype data from HapMap3 (consistent with the description in International HapMap 3 Consortium, Altshuler et al., Nature. 2010; 467(7311):52-58) using BEAGLE (consistent with the description in Browning et al., Am. J. Hum. Genet. 2007; 81(5):1084-1097). All association analyses were conducted using logistic regression in PLINK (consistent with the description in Purcell et al., Am. J. Hum. Genet. 2007; 81(3):559-575). Multidimensional scaling was performed on the entire data set, and each collection sample was analyzed separately using the first four multidimensional scaling components as covariates, to control for population substructure.

Genetic association analyses of ACO and IDH genes were performed in BD patients (sample set 1: n=1415, sample set 2: n=836) and controls (sample set 1: n=1271, sample set 2: n=2093). The call rates for all markers were >98%, and none showed marked departures from Hardy-Weinberg equilibrium. Across all single nucleotide polymorphisms (SNPs) tested, several SNPs within the ACO1 and IDH2 genes attained nominal significance, and none remained significant following multiple testing correction (Table 13).

TABLE 13

Genetic analyses of ACO and IDH genes in total samples (sample 1 and sample 2)

| | | Sample 1 | | | | | Sample 2 | | | |
|---|---|---|---|---|---|---|---|---|---|---|
| | SNP | Allele 1 | Allele 2 | OR | P | SNP | Allele 1 | Allele 2 | OR | P |
| ACO1 | rs10123372 | C | G | 0.885 | 0.152 | ACO1 rs10123372 | C | G | 1.1394 | 0.1415 |
| | rs1023087 | G | T | 0.984 | 0.812 | rs1023087 | G | T | 0.9027 | 0.164 |
| | rs10738890 | T | C | 1.03 | 0.608 | rs10738890 | T | C | 0.9636 | 0.5429 |
| | rs10813801 | A | G | 1.095 | 0.125 | rs10813801 | A | G | 1.0184 | 0.7656 |
| | rs10813808 | C | T | 0.899 | 0.107 | rs10813808 | C | T | 0.9136 | 0.1735 |
| | rs10813816 | T | C | 1.029 | 0.633 | rs10813816 | T | C | 0.8944 | 0.07373 |
| | rs10970971 | T | G | 1.102 | 0.117 | rs10970971 | T | G | 0.9478 | 0.3984 |
| | rs10970972 | C | T | 0.939 | 0.3000 | rs10970972 | C | T | 0.9226 | 0.1898 |
| | rs10970974 | A | C | 1.007 | 0.919 | rs10970974 | A | C | 1.0317 | 0.6593 |
| | rs10970978 | G | A | 1.09 | 0.375 | rs10970978 | G | A | 1.0056 | 0.9579 |
| | rs10970985 | C | G | 0.989 | 0.862 | rs10970985 | C | G | 0.9867 | 0.8397 |
| | rs10970986 | T | C | 1.037 | 0.562 | rs10970986 | T | C | 0.9303 | 0.2728 |
| | rs11793098 | A | G | 1.054 | 0.409 | rs11793098 | A | G | 1.1083 | 0.1227 |
| | rs12236816 | A | G | 0.91 | 0.436 | rs12236816 | A | G | 0.7645 | 0.03602 |
| | rs12985 | T | C | 0.991 | 0.87 | rs12985 | T | C | 0.8907 | 0.06049 |
| | rs13292540 | C | T | 1.13 | 0.046 | rs13292540 | C | T | 0.9531 | 0.4474 |
| | rs13302577 | G | A | 1.143 | 0.031 | rs13302577 | G | A | 0.9563 | 0.4895 |
| | rs17288067 | G | A | 1.023 | 0.764 | rs17288067 | G | A | 1.105 | 0.2111 |
| | rs17289116 | G | A | 0.98 | 0.777 | rs17289116 | G | A | 1.1019 | 0.1902 |
| | rs2375965 | A | G | 0.946 | 0.689 | rs2375965 | A | G | 0.9161 | 0.5804 |
| | rs3814521 | G | C | 1.041 | 0.529 | rs3814521 | G | C | 0.8615 | 0.02268 |
| | rs4442231 | T | C | 1.127 | 0.178 | rs4442231 | T | C | 0.8339 | 0.05335 |
| | rs4878497 | G | A | 1.007 | 0.901 | rs4878497 | G | A | 1.1116 | 0.0808 |
| | rs4879584 | C | T | 1.023 | 0.784 | rs4879584 | C | T | 1.0485 | 0.5667 |
| | rs4879586 | A | C | 1.019 | 0.779 | rs4879586 | A | C | 1.1563 | 0.03693 |
| | rs6476361 | A | G | 1.029 | 0.637 | rs6476361 | A | G | 0.8642 | 0.02495 |
| | rs7022554 | A | G | 0.993 | 0.903 | rs7022554 | A | G | 0.9605 | 0.5087 |
| | rs7026133 | C | T | 0.824 | 0.033 | rs7026133 | C | T | 0.7927 | 0.009586 |
| | rs7850888 | G | A | 1.055 | 0.467 | rs7850888 | G | A | 1.1319 | 0.1198 |
| | rs7866419 | A | C | 1.073 | 0.24 | rs7866419 | A | C | 1.0146 | 0.8133 |
| ACO2 | rs19573 | C | A | 1.021 | 0.78 | ACO2 rs19573 | C | A | 0.9311 | 0.3585 |
| | rs2076198 | T | G | 1.119 | 0.051 | rs2076198 | T | G | 1.0051 | 0.9342 |
| | rs2267436 | T | C | 1.042 | 0.593 | rs2267436 | T | C | 1.101 | 0.2405 |
| | rs738140 | A | G | 1.115 | 0.084 | rs738140 | A | G | 0.9276 | 0.2648 |
| | rs9611597 | A | T | 0.961 | 0.652 | rs9611597 | A | T | 0.9774 | 0.804 |
| | rs9611598 | G | A | 0.755 | 0.067 | rs9611598 | G | A | 1.333 | 0.08247 |

TABLE 13-continued

Genetic analyses of ACO and IDH genes in total samples (sample 1 and sample 2)

| | | Sample 1 | | | | | Sample 2 | | | |
|---|---|---|---|---|---|---|---|---|---|---|
| | SNP | Allele 1 | Allele 2 | OR | P | SNP | Allele 1 | Allele 2 | OR | P |
| IDH1 | rs11883490 | C | T | 0.894 | 0.185 | rs11883490 | C | T | 1.0224 | 0.7981 |
| | rs10202116 | T | C | 0.916 | 0.522 | rs10202116 | T | C | 0.7742 | 0.07785 |
| | rs6719638 | C | G | 0.949 | 0.555 | rs6719638 | C | G | 0.872 | 0.1599 |
| | rs10207062 | T | G | 1.04 | 0.513 | rs10207062 | T | G | 0.8867 | 0.04257 |
| | rs3769521 | G | A | 1.058 | 0.474 | rs3769521 | G | A | 0.9035 | 0.1856 |
| | rs12478635 | G | T | 0.863 | 0.07 | rs12478635 | G | T | 1.038 | 0.6544 |
| | rs13392540 | G | C | 0.891 | 0.139 | rs13392540 | G | C | 0.8904 | 0.1662 |
| IDH2 | rs11853055 | T | A | 0.939 | 0.279 | rs11853055 | T | A | 1.0216 | 0.7239 |
| | rs2970357 | T | C | 1.016 | 0.795 | rs2970357 | T | C | 1.023 | 0.705 |
| | rs9672249 | C | T | 1.183 | 0.015 | rs9672249 | C | T | 0.9865 | 0.8485 |
| | rs2970359 | A | G | 0.915 | 0.19 | rs2970359 | A | G | 0.9798 | 0.7656 |
| | rs4553601 | G | T | 1.073 | 0.336 | rs4553601 | G | T | 1.0398 | 0.607 |
| | rs7177165 | C | T | 1.025 | 0.698 | rs7177165 | C | T | 0.9851 | 0.8317 |
| | rs11073899 | G | A | 1.101 | 0.221 | rs11073899 | G | A | 0.9549 | 0.635 |
| | rs10520685 | G | A | 0.938 | 0.269 | rs10520685 | G | A | 0.9933 | 0.9113 |
| | rs8034938 | G | C | 1.048 | 0.564 | rs8034938 | G | C | 1.0256 | 0.76541 |
| | rs7178604 | A | G | 1.023 | 0.724 | rs7178604 | A | G | 0.9845 | 0.8235 |
| | rs3934860 | A | G | 1.148 | 0.089 | rs3934860 | A | G | 0.9274 | 0.3791 |
| | rs2970356 | C | G | 0.933 | 0.29 | rs2970356 | C | G | 0.9642 | 0.5891 |
| | rs9972327 | C | A | 1.083 | 0.309 | rs9972327 | C | A | 0.9788 | 0.8206 |
| IDH3A | rs11629561 | T | G | 1.001 | 0.991 | rs11629561 | T | G | 1.0878 | 0.168 |
| | rs11855354 | G | A | 0.98 | 0.73 | rs11855354 | G | A | 1.1057 | 0.09338 |
| | rs17850484 | G | A | 0.933 | 0.59 | rs17850484 | G | A | 0.9954 | 0.9711 |
| | rs7180687 | T | C | 0.905 | 0.194 | rs7180687 | T | C | 1.069 | 0.3651 |
| | rs3825847 | G | A | 0.919 | 0.557 | rs3825847 | G | A | 1.0476 | 0.7555 |
| | rs17674205 | A | G | 0.949 | 0.564 | rs17674205 | A | G | 0.9219 | 0.3589 |
| | rs11630013 | G | A | 0.958 | 0.577 | rs11630013 | G | A | 0.9676 | 0.6553 |
| | rs7165154 | C | G | 0.98 | 0.832 | rs7165154 | C | G | 0.9267 | 0.4238 |
| | rs2028548 | C | T | 0.951 | 0.429 | rs2028548 | C | T | 0.9475 | 0.3899 |
| | rs11072732 | T | C | 0.882 | 0.335 | rs11072732 | T | C | 1.1153 | 0.448 |
| | rs7179651 | C | G | 0.948 | 0.429 | rs7179651 | C | G | 1.1111 | 0.1197 |
| IDH3B | rs3818060 | T | G | 1.009 | 0.929 | rs3818060 | T | G | 1.0377 | 0.7384 |
| | rs4813587 | T | C | 0.983 | 0.771 | rs4813587 | T | C | 0.9595 | 0.4926 |
| | rs6051076 | G | T | 0.993 | 0.928 | rs6051076 | G | T | 1.0478 | 0.5565 |
| | rs6753 | T | C | 1.028 | 0.681 | rs6753 | T | C | 1.0592 | 0.4003 |
| | rs16987862 | A | G | 0.981 | 0.748 | rs16987862 | A | G | 0.9306 | 0.2485 |
| | rs1883977 | C | T | 0.997 | 0.963 | rs1883977 | C | T | 1.0167 | 0.819 |
| | rs6132905 | A | G | 0.971 | 0.684 | rs6132905 | A | G | 1.0607 | 0.4501 |
| | rs2073193 | C | G | 0.984 | 0.815 | rs2073193 | C | G | 0.9536 | 0.48 |
| | rs742847 | G | A | 0.991 | 0.884 | rs742847 | G | A | 0.9898 | 0.8678 |
| | rs2422824 | T | C | 0.994 | 0.923 | rs2422824 | T | C | 0.9656 | 0.5643 |

Epistasis tests were also conducted in PLINK separately by sample using the directly genotyped markers. Interactions between the markers within the sets of IDH and ACO genes were tested, yielding 272 tests in sample 1 and 152 tests in sample 2. Epistasis tests were conducted separately in the two sample sets. The compelling interactions in both sample sets were detected between markers in the ACO1 and IDH2 genes (sample set 1: P=0.0065 for rs10970986 and rs2970357; sample set 2: P=0.0025 for rs13302577 and rs2970359) (Table 14).

TABLE 14

Epistatic effects of ACO and IDH genes in sample 1 and sample 2

| | Gene 1 | CHR1 | SNP1 | Gene 2 | CHR2 | SNP2 | Interaction OR | $X^2$ | P |
|---|---|---|---|---|---|---|---|---|---|
| Sample 1 | ACO1 | 9 | rs10970986 | IDH2 | 15 | rs2970357 | 0.80 | 7.41 | 0.0065 |
| | ACO1 | 9 | rs10970972 | IDH2 | 15 | rs4553601 | 0.78 | 5.85 | 0.0156 |
| | ACO1 | 9 | rs10813816 | IDH2 | 15 | rs2970357 | 0.83 | 5.29 | 0.0214 |
| | ACO1 | 9 | rs4442231 | IDH2 | 15 | rs2970359 | 1.38 | 5.17 | 0.0229 |
| | ACO1 | 9 | rs4442231 | IDH2 | 15 | rs2970357 | 1.30 | 4.69 | 0.0303 |
| | ACO2 | 22 | rs9611598 | IDH2 | 15 | rs9672249 | 0.56 | 4.61 | 0.0317 |
| | ACO1 | 9 | rs10813801 | IDH2 | 15 | rs4553601 | 0.81 | 4.59 | 0.0321 |
| | ACO1 | 9 | rs4879586 | IDH2 | 15 | rs10520685 | 0.82 | 4.57 | 0.0326 |
| | ACO1 | 9 | rs6476361 | IDH2 | 15 | rs2970357 | 1.19 | 4.30 | 0.0381 |
| | ACO1 | 9 | rs12985 | IDH2 | 15 | rs11073899 | 1.23 | 3.91 | 0.0480 |
| Sample 2 | ACO1 | 9 | rs13302577 | IDH2 | 15 | rs2970359 | 0.74 | 9.13 | 0.0025 |
| | ACO2 | 22 | rs9611598 | IDH3A | 15 | rs2028548 | 0.53 | 5.59 | 0.0181 |
| | ACO1 | 9 | rs13292540 | IDH1 | 2 | rs3769521 | 1.31 | 5.52 | 0.0188 |
| | ACO1 | 9 | rs13302577 | IDH1 | 2 | rs3769521 | 1.31 | 5.42 | 0.0199 |
| | ACO1 | 9 | rs13292540 | IDH2 | 15 | rs2970359 | 0.81 | 4.66 | 0.0308 |

TABLE 14-continued

Epistatic effects of ACO and IDH genes in sample 1 and sample 2

| Gene 1 | CHR1 | SNP1 | Gene 2 | CHR2 | SNP2 | Interaction OR | $X^2$ | P |
|---|---|---|---|---|---|---|---|---|
| ACO1 | 9 | rs7866419 | IDH2 | 15 | rs2970359 | 1.23 | 4.62 | 0.0316 |
| ACO1 | 9 | rs13292540 | IDH3A | 15 | rs7180687 | 1.24 | 4.01 | 0.0452 |
| ACO1 | 9 | rs10813816 | IDH3A | 15 | rs17674205 | 0.78 | 3.89 | 0.0485 |

Altered isocitrate metabolism does not appear to result from primary genetic changes, because SNPs in the ACO and IDH genes were not associated with BD in the Swedish population.

Example 6

Effects of lithium (Li) and valproic acid (VPA) on rat CSF levels were studied in this example. This example demonstrates that biomarkers of the present invention can be used independent of whether a subject is taking an existing bipolar disorder medication.

In order to examine the effects of medication on the metabolites such as isocitrate, metabolomics analyses of CSF samples from rats treated with chronic (4-weeks) treatment of Li or VPA were performed. The CSF concentrations of 116 major metabolites from several pathways were measured. Sixty four substances were detected in the rat CSF. Male Sprague-Dawley rats (Japan SLC Inc., Shizuoka, Japan) aged 6 weeks old were used in this study. All rats were housed in groups of three per cage in a room maintained at 23° C.±2° C. and 60±10% humidity with a 12/12 hour light/dark cycle (lights on at 7:00 a.m.). The rats were given free access to food and water. Animal care and use were conducted in accordance with the Institutional Guidelines for Animal Care and Use of Otsuka Pharmaceutical Co., Ltd. (Tokushima, Japan). Animals were divided into three groups (n=5-6), with the treatment group receiving lithium carbonate (Li; 600 mg/L, Wako Pure Chemical Industries, Ltd., Osaka, Japan) or valproic acid sodium salt (VPA: 4 g/L, Sigma-Aldrich Co., Tokyo, Japan) via drinking water, and the control group receiving vehicle (water) for 4 weeks (day 1-day 28). The drinking water was replaced twice a week. The doses of Li and VPA were selected based on the doses that were previously reported (consistent with the description in Talab et al., Eur J Pharmacol. 2010; 647(1-3):171-177; and Niles et al., Int J Neuropsychopharmacol. 2012; 15 (9):1343-1350, which are incorporated in their entireties by reference herein). All animals were decapitated on day 30 after CSF sampling, and brain regions (prefrontal cortex, and hippocampus) were dissected rapidly on ice. Metabolomic analyses of rat CSF samples were performed as described herein.

Treatment with Li significantly increased CSF levels of succinic acid and argininosuccinic acid. On the other hand, treatment with VPA significantly altered CSF levels of threonine, glutamine, arginine, tryptophan and argininosuccinic acid (Table 15). Thus, CSF levels of isocitrate in rats were not altered by chronic treatment with Li or VPA.

TABLE 15

Metabolomics data of rat CSF samples

| | Control (N = 6) | | | Lithium (N = 6) | | | Valproic acid (N = 6) | | | Lithium vs Control | VPA vs Control | One-way ANOVA |
|---|---|---|---|---|---|---|---|---|---|---|---|---|
| Compound name | Mean (μM) | S.D. | N | Mean (μM) | S.D. | N | Mean (μM) | S.D. | N | P-value[ǁ] | P-value[ǁ] | P-value |
| Nicotinamide Adenine dinucleotide (NAD+) | 0.8 | 0.00 | 6 | 0.8 | 0.05 | 6 | 0.8 | 0.0 | 5 | | | |
| cyclic AMP (cAMP) | 0.007 | 1.2E-03 | 5 | 0.007 | 1.2E-03 | 5 | 0.006 | 0.002 | 6 | | | |
| cyclic GMP (cGMP) | 0.003 | 0.002 | 6 | 0.003 | 5.5E-04 | 6 | 0.003 | 5.0E-04 | 4 | | | |
| Xanthine | 1.4 | 0.2 | 6 | 1.6 | 0.12 | 6 | 1.5 | 0.1 | 5 | | | |
| ADP-ribose | 0.012 | 0.004 | 6 | 0.010 | 1.2E-03 | 6 | 0.01 | 0.00 | 5 | | | |
| Mevalonic acid | N.D. | N.A. | 0 | 0.003 | N.A. | 1 | N.D. | N.A. | 0 | | | |
| UDP-glucose | 0.3 | 0.00 | 6 | 0.3 | 0.000 | 4 | 0.3 | 0.00 | 3 | | | |
| Uric acid | 1.6 | 0.3 | 6 | 1.8 | 0.5 | 6 | 1.8 | 0.2 | 5 | | | |
| Nicotinamide Adenine dinucleotide phophate (NADP+) | 0.09 | N.A. | 1 | 0.09 | 0.007 | 2 | 0.09 | 0.0E+00 | 3 | | | |
| Inosine monophosphate (IMP) | 0.10 | 0.02 | 6 | 0.10 | 0.05 | 6 | 0.1 | 0.1 | 4 | | | |
| Glucose 6-phosphate | 0.6 | 0.08 | 6 | 0.5 | 0.10 | 6 | 0.5 | 0.1 | 5 | | | |
| Fructose 6-phosphate | 0.2 | 0.05 | 6 | 0.2 | 0.04 | 6 | 0.2 | 0.0 | 5 | | | |
| Ribose 5-phosphate | 0.07 | 0.015 | 6 | 0.07 | 0.014 | 6 | 0.06 | 0.02 | 5 | | | |
| Ribulose 5-phosphate | 0.11 | 0.03 | 5 | 0.10 | 0.03 | 5 | 0.08 | 0.02 | 4 | | | |
| Glyceraldehyde 3-phosphate | 0.6 | 0.4 | 6 | 0.9 | 0.5 | 6 | 1.1 | 0.2 | 5 | | | |
| Phosphocreatine | 6.6 | 0.9 | 5 | 6.9 | 1.2 | 6 | 6.8 | 1.6 | 5 | | | |
| Dihydroxyacetone phosphate | 0.4 | 0.4 | 6 | 0.6 | 0.4 | 6 | 0.8 | 0.2 | 5 | | | |
| N-Carbamoylaspartic acid | 0.03 | 0.006 | 6 | 0.04 | 0.005 | 6 | 0.02 | 0.004 | 5 | | | |
| 3-Phosphoglyceric acid | 0.3 | 0.05 | 6 | 0.3 | 0.10 | 6 | 0.3 | 0.08 | 5 | | | |
| Phosphoenolpyruvic acid | 0.04 | 0.007 | 2 | 0.2 | 0.2 | 4 | 0.15 | 0.05 | 3 | | | |
| Adenosine monophosphate (AMP) | 0.06 | N.A. | 1 | N.D. | N.A. | 0 | N.D. | N.A. | 0 | | | |
| 2-Oxoisovaleric acid | 4.2 | 0.4 | 6 | 4.3 | 0.4 | 6 | 4.3 | 0.5 | 5 | | | |

TABLE 15-continued

Metabolomics data of rat CSF samples

| Compound name | Control (N = 6) Mean (μM) | S.D. | N | Lithium (N = 6) Mean (μM) | S.D. | N | Valproic acid (N = 6) Mean (μM) | S.D. | N | Lithium vs Control P-value ‖ | VPA vs Control P-value ‖ | One-way ANOVA P-value |
|---|---|---|---|---|---|---|---|---|---|---|---|---|
| Lactic acid | 2,194 | 231 | 6 | 2,438 | 76 | 6 | 2,361 | 194 | 5 | | | |
| Guanosine triphosphate (GTP) | 0.4 | N.A. | 1 | N.D. | N.A. | 0 | N.D. | N.A. | 0 | | | |
| Glycerol 3-phosphate | 6.7 | 0.7 | 6 | 7.2 | 0.8 | 6 | 7.0 | 0.7 | 5 | | | |
| Pyruvic acid | 31 | 4.3 | 6 | 29 | 2.9 | 6 | 21 | 7.3 | 5 | | | |
| Succinic acid | 7.1 | 0.7 | 6 | 9.0 | 0.5 | 6 | 7.4 | 1.4 | 5 | 0.005 | 0.810 | $F_{(2, 14)} = 7.6$, $P = 0.0058$ |
| Malic acid | 0.7 | 0.5 | 5 | 2.2 | 1.3 | 5 | 0.7 | 0.8 | 2 | | | |
| Citric acid | 40 | 9.5 | 6 | 57 | 8.5 | 6 | 44 | 13 | 5 | | | |
| Isocitric acid | 0.9 | 0.5 | 6 | 2.0 | 0.9 | 6 | 1.6 | 1.2 | 5 | | | |
| Urea | 3,918 | 397 | 6 | 4,332 | 281 | 6 | 3,714 | 129 | 5 | | | |
| Glycine (Gly) | 5.7 | 0.9 | 6 | 5.5 | 0.7 | 6 | 6.5 | 0.4 | 5 | | | |
| Alanin (Ala) | 55 | 2.1 | 6 | 54 | 5.3 | 6 | 50 | 1.3 | 5 | | | |
| Choline | 7.2 | 1.2 | 6 | 7.5 | 0.9 | 6 | 7.8 | 1.4 | 5 | | | |
| Serine (Ser) | 79 | 5.0 | 6 | 82 | 5.6 | 6 | 83 | 3.8 | 5 | | | |
| Creatinine | 5.7 | 3.1 | 6 | 6.0 | 3.9 | 6 | 6.2 | 4.9 | 5 | | | |
| Valine (Val) | 2.2 | 0.4 | 6 | 2.3 | 0.3 | 6 | 2.1 | 0.4 | 5 | | | |
| Homoserine | 0.10 | 0.03 | 6 | 0.10 | 0.05 | 6 | 0.09 | 0.05 | 5 | | | |
| Threonine (Thr) | 56 | 4.8 | 6 | 54 | 3.1 | 6 | 41 | 4.0 | 5 | 0.795 | 5.0E+00 | $F_{(2, 14)} = 21.53$, $P < .0001$ |
| Hydroxyproline | 1.2 | 0.12 | 6 | 1.1 | 0.05 | 6 | 1.1 | 0.08 | 5 | | | |
| Creatine | 62 | 3.1 | 6 | 60 | 3.9 | 6 | 56 | 5 | 5 | | | |
| Leucine (Leu) | 4.9 | 0.3 | 6 | 5.1 | 0.4 | 6 | 4.5 | 0.3 | 5 | | | |
| Isoleucine (Ile) | 1.3 | 0.11 | 6 | 1.5 | 0.15 | 6 | 1.2 | 0.1 | 5 | | | |
| Asparagine (Asn) | 4.7 | 0.5 | 6 | 4.8 | 0.3 | 6 | 4.0 | 0.2 | 5 | | | |
| Ornithine | 2.4 | 0.2 | 6 | 2.3 | 0.1 | 6 | 2.2 | 0.13 | 5 | | | |
| Aspargic acid (Asp) | 1.8 | 0.14 | 2 | 1.8 | 0.10 | 3 | 1.6 | 0.1 | 2 | | | |
| Hypoxanthine | 1.1 | 0.08 | 6 | 1.2 | 0.4 | 6 | 1.4 | 0.3 | 5 | | | |
| Glutamine (Gln) | 558 | 17 | 6 | 534 | 26 | 6 | 598 | 30 | 5 | 0.189 | 0.034 | $F_{(2, 14)} = 9.31$, $P = 0.0027$ |
| Lysine (Lys) | 75 | 11 | 6 | 71 | 11 | 6 | 85 | 9 | 5 | | | |
| Glutamic acid (Glu) | 2.1 | 0.5 | 6 | 2.0 | 0.2 | 6 | 1.6 | 0.3 | 5 | | | |
| Methionine (Met) | 3.8 | 0.6 | 6 | 4.4 | 0.6 | 6 | 3.3 | 0.04 | 5 | | | |
| Histidine (His) | 7.0 | 0.4 | 6 | 7.1 | 0.6 | 6 | 7.1 | 0.3 | 5 | | | |
| Phenylalanine (Phe) | 2.9 | 0.2 | 6 | 3.1 | 0.2 | 6 | 2.9 | 0.2 | 5 | | | |
| Arginine (Arg) | 35 | 2.1 | 6 | 31 | 2.9 | 6 | 27 | 3.9 | 5 | 0.054 | 0.002 | $F_{(2, 14)} = 9.00$, $P = 0.0031$ |
| Citrulline | 3.6 | 0.2 | 6 | 3.8 | 0.7 | 6 | 3.6 | 0.5 | 5 | | | |
| Tyrosine (Tyr) | 5.2 | 0.7 | 6 | 5.4 | 0.9 | 6 | 5.2 | 0.6 | 5 | | | |
| Tryptophan (Trp) | 1.2 | 0.15 | 6 | 1.2 | 0.05 | 6 | 1.0 | 0.04 | 5 | 0.417 | 0.013 | $F_{(2, 14)} = 9.57$, $P = 0.0024$ |
| Carnosine | 0.6 | 0.05 | 6 | 0.5 | 0.04 | 5 | 0.5 | 0.1 | 4 | | | |
| Adenosine | 0.2 | 0.00 | 6 | 0.2 | 0.03 | 4 | 0.2 | 0.00 | 3 | | | |
| Argininosuccinic acid | 0.9 | 0.10 | 6 | 1.0 | 0.04 | 6 | 0.7 | 0.09 | 5 | 0.049 | 0.042 | $F_{(2, 14)} = 12.08$ $P = 0.0009$ |
| Glutathione (GSSG) | 1.0 | 0.4 | 6 | 1.1 | 0.2 | 6 | 0.9 | 0.3 | 5 | | | |
| S-Adenosylmethionine | 0.4 | 0.05 | 6 | 0.5 | 0.05 | 6 | 0.5 | 0.05 | 5 | | | |

Number in the N column was the sample number which can detect.

Example 7

Effects of lithium (Li) and valproic acid (VPA) on rat serum levels were studied in this example. This example demonstrates that biomarkers of the present invention can be used independent of whether a subject is taking an existing bipolar disorder medication.

In order to examine the effects of medication on the six metabolites, such as pyruvic acid, N-acetylglutamic acid, 2-oxoglutaric acid, β-alanine, serine, and arginine, metabolomics analyses of serum samples from rats treated with chronic (4-weeks) treatment of Li or VPA were performed. The serum concentrations of 116 major metabolites from several pathways were measured. Seventy three substances were detected in the rat serum. Among the above six metabolites, treatment with Li significantly increased serum levels of 2-oxoglutaric acid. Thus, serum levels of pyruvic acid, N-acetylglutamic acid, β-alanine, serine, and arginine in rats were not altered by chronic treatment with Li or VPA (Table 16).

Based on the results in Examples 6 and 7, chronic (4-weeks) treatment of Li or VPA did not alter CSF levels of isocitrate in the rats or the expression of mRNA of Aco1, Aco2, Idh3a and Idh3b in the prefrontal cortex and hippocampus of rat brain, suggesting that Li and VPA do not affect the synthesis and metabolism of isocitrate in the brain. Therefore, it is unlikely that these mood stabilizers affect CSF levels of isocitrate in BD patients.

TABLE 16

Metabolomics data of rat serum samples

| Compound name | Control | | | Li | | | VPA | | | Li vs Control P Value | VPA vs Control P Value | One-way ANOVA P-value |
|---|---|---|---|---|---|---|---|---|---|---|---|---|
| | Mean | S.D. | N | Mean | S.D. | N | Mean | S.D. | N | | | |
| NAD+ | 1.1 | 0.03 | 6 | 1.1 | 0.05 | 6 | 1.1 | 0.04 | 5 | | | |
| cAMP | 0.04 | 0.007 | 6 | 0.04 | 0.006 | 6 | 0.05 | 0.011 | 6 | | | |
| cGMP | 0.02 | 0.004 | 6 | 0.02 | 0.004 | 6 | 0.02 | 0.004 | 6 | | | |
| ADP-ribose | 0.2 | 0.2 | 6 | 0.2 | 0.12 | 6 | 0.13 | 0.06 | 6 | | | |
| Mevalonic acid | 0.07 | 0.02 | 5 | 0.05 | 0.03 | 6 | 1.5E−04 | N.A. | 1 | | | |
| UDP-glucose | 0.6 | 0.2 | 6 | 0.6 | 0.06 | 6 | 0.6 | 0.05 | 5 | | | |
| Uric acid | 24 | 5.2 | 6 | 23 | 8.3 | 6 | 25 | 9.5 | 6 | | | |
| IMP | 0.2 | 0.04 | 5 | 0.14 | 0.012 | 6 | 0.13 | 0.008 | 3 | | | |
| Glucose 6-phosphate | 0.8 | 0.7 | 6 | 0.6 | 0.3 | 6 | 0.6 | 0.11 | 6 | | | |
| Fructose 6-phosphate | 0.12 | 0.14 | 6 | 0.10 | 0.07 | 6 | 0.09 | 0.03 | 6 | | | |
| Ribose 5-phosphate | 0.04 | 0.05 | 5 | 0.04 | 0.04 | 6 | 0.04 | 0.04 | 5 | | | |
| Ribose 1-phosphate | 1.4 | 1.7 | 2 | 0.3 | 0.3 | 4 | 0.4 | 0.4 | 6 | | | |
| Ribulose 5-phosphate | 0.2 | 0.05 | 6 | 0.2 | 0.04 | 6 | 0.2 | 0.03 | 4 | | | |
| Phosphocreatine | 0.7 | 0.2 | 6 | 0.7 | 0.09 | 6 | 0.9 | 0.2 | 6 | 0.8390 | 0.0291 | $F_{(2, 15)}$ = 5.99, P = 0.0122 |
| Fructose 1,6-diphosphate | 0.3 | 0.04 | 5 | 0.3 | 0.03 | 6 | 0.3 | 0.03 | 6 | | | |
| N-Carbamoylaspartic acid | 0.02 | 0.005 | 6 | 0.02 | 0.006 | 6 | 0.02 | 0.004 | 6 | | | |
| 2-Phosphoglyceric acid | 0.7 | 0.2 | 6 | 0.7 | 0.15 | 6 | 0.6 | 0.2 | 6 | | | |
| 2,3-Diphosphoglyceric acid | 2.7 | 0.7 | 6 | 2.3 | 0.7 | 6 | 2.1 | 0.5 | 6 | | | |
| 3-Phosphoglyceric acid | 5.0 | 0.9 | 6 | 5.5 | 1.2 | 6 | 5.0 | 0.9 | 6 | | | |
| GMP | 0.5 | 0.3 | 2 | 0.12 | 0.2 | 4 | 0.07 | 0.06 | 4 | | | |
| AMP | 0.7 | 0.7 | 6 | 0.5 | 0.4 | 6 | 0.4 | 0.2 | 6 | | | |
| 2-Oxoisovaleric acid | 11 | 3.1 | 6 | 12 | 1.9 | 6 | 15 | 3.1 | 6 | | | |
| GDP | 0.4 | 0.05 | 2 | 0.5 | N.A. | 1 | 0.4 | N.A. | 1 | | | |
| Lactic acid | 3,263 | 917 | 6 | 2,764 | 554 | 6 | 2,751 | 435 | 6 | | | |
| GTP | 1.9 | 0.06 | 5 | 2.0 | 0.08 | 4 | 1.9 | 0.06 | 2 | | | |
| ATP | 4.3 | 0.15 | 6 | 4.3 | 0.2 | 6 | 4.2 | 0.10 | 6 | | | |
| Glycerol 3-phosphate | 3.5 | 0.8 | 6 | 3.1 | 0.5 | 6 | 3.5 | 0.2 | 6 | | | |
| Glycolic acid | 10 | 1.8 | 5 | 9.4 | 0.9 | 6 | 11 | 1.2 | 6 | | | |
| Pyruvic acid | 113 | 37 | 6 | 126 | 31 | 6 | 107 | 20 | 6 | | | |
| 2-Hydroxyglutaric acid | 1.7 | 0.6 | 6 | 2.7 | 0.6 | 6 | 1.5 | 0.2 | 6 | 0.0029 | 0.7833 | $F_{(2, 15)}$ = 11.65, P = 0.0009 |
| Succinic acid | 16 | 6.3 | 6 | 17 | 4.7 | 6 | 10 | 2.1 | 6 | | | |
| Malic acid | 12 | 3.7 | 6 | 23 | 7.9 | 6 | 12 | 6.2 | 6 | 0.0152 | 0.9988 | $F_{(2, 15)}$ = 6.26, P = 0.0105 |
| 2-Oxoglutaric acid | 31 | 7.7 | 6 | 64 | 17 | 6 | 29 | 6.1 | 6 | 0.0003 | 0.9445 | $F_{(2, 15)}$ = 17.36, P = 0.0001 |
| Fumaric acid | 2.4 | 0.7 | 6 | 4.0 | 1.2 | 6 | 2.6 | 1.1 | 6 | 0.0235 | 0.9174 | $F_{(2, 15)}$ = 4.76, P = 0.0251 |
| Citric acid | 171 | 11 | 6 | 212 | 24 | 6 | 151 | 4.2 | 6 | 0.0006 | 0.0656 | $F_{(2, 15)}$ = 25.07, P < 0.0001 |
| cis-Aconitic acid | 3.6 | 0.5 | 6 | 4.3 | 0.7 | 6 | 3.1 | 0.2 | 6 | | | |
| Isocitric acid | 9.1 | 2.8 | 6 | 9.5 | 3.7 | 6 | 8.2 | 1.5 | 6 | | | |
| Urea | 5,551 | 686 | 6 | 6,360 | 880 | 6 | 5,050 | 364 | 6 | | | |
| Gly | 340 | 46 | 6 | 340 | 34 | 6 | 488 | 51 | 6 | 1.0000 | <0.0001 | $F_{(2, 15)}$ = 22.52, P < 0.0001 |
| Putrescine | 0.5 | 0.2 | 4 | 0.4 | 0.13 | 4 | 0.3 | 0.015 | 2 | | | |
| Ala | 676 | 97 | 6 | 671 | 80 | 6 | 757 | 70 | 6 | | | |
| Sarcosine | 6.4 | 1.6 | 6 | 7.2 | 2.0 | 6 | 5.5 | 1.1 | 6 | | | |
| β-Ala | 2.3 | 0.7 | 6 | 2.0 | 0.3 | 6 | 1.9 | 0.3 | 6 | | | |
| N,N-Dimethylglycine | 17 | 2.8 | 6 | 18 | 4.2 | 6 | 11 | 1.5 | 6 | 0.7994 | 0.0184 | $F_{(2, 15)}$ = 7.12, P = 0.0067 |
| Choline | 14 | 3.7 | 6 | 15 | 3.5 | 6 | 13 | 2.6 | 6 | | | |
| Ser | 297 | 41 | 6 | 319 | 34 | 6 | 319 | 34 | 6 | | | |
| Carnosine | 0.13 | N.A. | 1 | 0.2 | 0.07 | 3 | 0.2 | 0.05 | 2 | | | |
| Creatinine | 25 | 1.6 | 6 | 26 | 2.3 | 6 | 25 | 2.9 | 6 | 0.3994 | 0.0176 | $F_{(2, 15)}$ = 9.23, P = 0.0024 |
| Pro | 244 | 33 | 6 | 272 | 36 | 6 | 220 | 15 | 6 | | | |
| Betaine | 199 | 20 | 6 | 259 | 44 | 6 | 287 | 49 | 6 | 0.0367 | 0.0032 | $F_{(2, 15)}$ = 7.61, P = 0.0052 |

TABLE 16-continued

Metabolomics data of rat serum samples

| Compound name | Control Mean | Control S.D. | Control N | Li Mean | Li S.D. | Li N | VPA Mean | VPA S.D. | VPA N | Li vs Control P Value | VPA vs Control P Value | One-way ANOVA P-value |
|---|---|---|---|---|---|---|---|---|---|---|---|---|
| Val | 290 | 26 | 6 | 283 | 18 | 6 | 290 | 29 | 6 | | | |
| Thr | 292 | 55 | 6 | 298 | 30 | 6 | 217 | 21 | 6 | 0.9509 | 0.0068 | $F_{(2, 15)} =$ 8.55, $P =$ 0.0033 |
| Hydroxyproline | 72 | 18 | 6 | 65 | 11 | 6 | 65 | 14 | 6 | | | |
| Creatine | 135 | 22 | 6 | 104 | 31 | 6 | 211 | 67 | 6 | | | |
| Ile | 118 | 15 | 6 | 119 | 9.7 | 6 | 119 | 9.9 | 6 | | | |
| Leu | 205 | 21 | 6 | 199 | 14 | 6 | 207 | 14 | 6 | | | |
| Asn | 87 | 11 | 6 | 87 | 7.4 | 6 | 77 | 7.3 | 6 | | | |
| Ornithine | 95 | 59 | 6 | 75 | 22 | 6 | 76 | 12 | 6 | | | |
| Asp | 12 | 2.2 | 6 | 13 | 1.8 | 6 | 12 | 1.6 | 6 | | | |
| Gln | 887 | 41 | 6 | 817 | 59 | 6 | 1,001 | 49 | 6 | 0.0551 | 0.0026 | $F_{(2, 15)} =$ 20.28, $P <$ 0.0001 |
| Lys | 504 | 75 | 6 | 468 | 88 | 6 | 696 | 215 | 6 | | | |
| Glu | 126 | 16 | 6 | 140 | 17 | 6 | 173 | 19 | 6 | 0.3312 | 0.0006 | $F_{(2, 15)} =$ 11.49, $P =$ 0.0009 |
| Met | 53 | 3.5 | 6 | 59 | 8.7 | 6 | 53 | 4.5 | 6 | | | |
| His | 88 | 7.3 | 6 | 89 | 4.6 | 6 | 90 | 3.6 | 6 | | | |
| Carnitine | 76 | 12 | 6 | 65 | 7.8 | 6 | 78 | 6.9 | 6 | | | |
| Phe | 66 | 4.4 | 6 | 67 | 3.1 | 6 | 65 | 6.9 | 6 | | | |
| Arg | 210 | 57 | 6 | 206 | 27 | 6 | 206 | 27 | 6 | | | |
| Citrulline | 96 | 14 | 6 | 103 | 16 | 6 | 92 | 9.3 | 6 | | | |
| Tyr | 95 | 18 | 6 | 95 | 17 | 6 | 89 | 10 | 6 | | | |
| Trp | 142 | 12 | 6 | 148 | 9.8 | 6 | 110 | 8.8 | 6 | 0.4683 | 0.0002 | $F_{(2, 15)} =$ 23.60, $P <$ 0.0001 |
| Cystathionine | 1.3 | 0.2 | 3 | 1.2 | 0.06 | 4 | 1.1 | N.A. | 1 | | | |
| Argininosuccinic acid | 0.5 | 0.13 | 4 | 0.6 | 0.15 | 6 | 0.4 | 9.0E-04 | 2 | | | |
| Glutathione (GSSG) | 0.7 | 0.7 | 6 | 0.5 | 0.3 | 6 | 0.4 | 0.12 | 6 | | | |

Number in the N column was the sample number which can detect.

Example 8

Effects of lithium (Li) and valproic acid (VPA) on, expression of Aco1, Aco2, Idh3a, and Idh3b genes in the rat brain were studied. This example demonstrates that substrates, products, and/or enzymes of isocitrate metabolism can be used as biomarkers and/or for screening independent of whether a subject is taking an existing bipolar disorder medication. This example also demonstrates that subunits of isocitrate dehydrogenase 3 (IDH3) can be used as therapeutic targets, as well as biomarker and screening tools independent of whether a subject is taking an existing bipolar disorder medication.

Prefrontal cortex, and hippocampus were dissected rapidly on ice and stored in RNA later (Applied Biosystems) at 4° C. until used for RNA isolation, cDNA synthesis and polymerase chain reaction (PCR) amplification. The total RNA was extracted using the RNeasy Lipid Tissue Mini Kit (QIAGEN) following the instructions of manufacturer. RNA yield and integrity was assessed using Nanodrop (NanoDrop Technologies). Reverse transcription of total RNA was done using the SUPERSCRIPT VILO cDNA Synthesis Kit (Invitrogen). In the quantitative PCR, the cDNA was amplified using commercial TaqMan assays (Applied Biosystems) for rat Idh3A (Rn00586270_m1), Idh3B (Rn00504589_g1), Aco1 (Rn00569045_m1), Aco2 (Rn00577876_m1) and Gapdh (Rn01775763_g1) with an ABI 7500 Fast Real-Time PCR system (Applied Biosystems). (Table 17) Reactions were performed in triplicates. All reactions were normalized to Gapdh and presented as relative expression changes compared to control.

TABLE 17

Informations of IDH and ACO genes for RT-PCR analysis
<Rat brain samples>

| Gene Symbol | Assay ID | RefSeq | Gene Name |
|---|---|---|---|
| Gapdh | Rn01775763_g1 | NM_017008.3 | glyceraldehyde-3-phosphate dehydrogenase |
| Idh3a | Rn00586270_m1 | NM_053638.1 | isocitrate dehydrogenase 3 (NAD+) alpha |
| Idh3b | Rn00504589_g1 | NM_053581.1 | isocitrate dehydrogenase 3 (NAD+) beta |
| Aco1 | Rn00569045_m1 | NM_017321.1 | aconitase 1, soluble |
| Aco2 | Rn00577876_m1 | NM_024398.2 | aconitase 2, mitochondrial |

The mRNA levels of Aco1, Aco2, Idh3a and Idh3b in the prefrontal cortex and hippocampus were not altered by treatment of Li or VPA (Table 18). These results show that chronic treatment of Li and VPA did not affect the expression of mRNA for Aco1, Aco2, Idh3a and Idh3b in the prefrontal cortex and hippocampus of rats.

TABLE 18

Effects of lithium and valproic acid on the gene expression of Aco and Idh in the rat prefrontal cortex and hippocampus

| Parameter | Controls (n = 6) | Lithium (n = 6) | Valproic acid (n = 6) | One-way ANOVA |
|---|---|---|---|---|
| <Prefrontal cortex> | | | | |
| Aco1 | 1.000 ± 0.0835 | 1.0091 ± 0.1737 | 1.1550 ± 0.1237 | $F(2, 14) = 1.51, P = 0.2539$ |
| Aco2 | 1.000 ± 0.1266 | 0.9921 ± 0.1576 | 0.9505 ± 0.1596 | $F(2, 14) = 0.16, P = 0.8513$ |
| Idh3a | 1.000 ± 0.1735 | 1.3420 ± 0.5725 | 1.2546 ± 0.3578 | $F(2, 14) = 1.41, P = 0.2760$ |
| Idh3b | 1.000 ± 0.1024 | 1.3440 ± 0.4424 | 1.2265 ± 0.2128 | $F(2, 14) = 2.08, P = 0.1619$ |
| <Hippocampus> | | | | |
| Aco1 | 1.000 ± 0.0435 | 1.0171 ± 0.0497 | 1.0956 ± 0.0520 | $F(2, 14) = 3.19, P = 0.0720$ |
| Aco2 | 1.000 ± 0.0708 | 1.1340 ± 0.1248 | 1.0358 ± 0.0499 | $F(2, 14) = 2.13, P = 0.1552$ |
| Idh3a | 1.000 ± 0.1317 | 1.2250 ± 0.2326 | 1.0302 ± 0.1963 | $F(2, 14) = 1.43, P = 0.2732$ |
| Idh3b | 1.000 ± 0.0515 | 1.3074 ± 0.2494 | 1.1512 ± 0.1377 | $F(2, 14) = 2.11, P = 0.1582$ |

The data are the mean ± SD.

The present invention includes the following aspects/embodiments/features in any order and/or in any combination:

1. The present invention relates to a method of diagnosing, confirming a diagnosis of, or determining a predisposition for a bipolar disorder in a subject, the method comprising:
measuring an amount of at least one of the following biomarkers,
 isocitric acid in a cerebrospinal fluid sample collected from the subject,
 cis-aconitic acid in a cerebrospinal fluid sample collected from the subject,
 pyruvic acid in a serum sample collected from the subject,
 N-acetylglutamic acid in a serum sample collected from the subject,
 2-oxoglutaric acid in a serum sample collected from the subject,
 β-alanine in a serum sample collected from the subject,
 arginine in a serum sample collected from the subject,
 serine in a serum sample collected from the subject,
 uric acid in a serum sample collected from the subject, and
 citric acid in a serum sample collected from the subject; and
comparing the amount of the at least one biomarker with a control amount of the at least one biomarker in a corresponding sample collected from a subject without the bipolar disorder,
wherein an increase in the amount of isocitric acid, an increase in the amount of cis-aconitic acid, an increase in the amount of pyruvic acid, an increase in the amount of N-acetylglutamic acid, an increase in the amount of 2-oxoglutaric acid, a decrease in the amount of β-alanine, a decrease in the amount of arginine, a decrease in the amount of serine, an increase in the amount of uric acid, and a decrease in the amount of citric acid, in comparison to the control amount of the at least one biomarker are indicative that the subject has the bipolar disorder or a predisposition for the bipolar disorder.

2. The method of any preceding or following embodiment/feature/aspect, wherein the at least one biomarker comprises isocitric acid in the cerebrospinal fluid sample collected from a subject.

3. The method of any preceding or following embodiment/feature/aspect, wherein the at least one biomarker further comprises serine in a serum sample collected from the subject.

4. The method of any preceding or following embodiment/feature/aspect, wherein the at least one biomarker comprises at least one of the biomarkers collected from cerebrospinal fluid and at least one of the biomarkers collected from serum in combination.

5. The method of any preceding or following embodiment/feature/aspect, wherein at least two of the biomarkers are measured in combination.

6. The method of any preceding or following embodiment/feature/aspect, wherein at least five of the biomarkers are measured in combination.

7. The method of any preceding or following embodiment/feature/aspect, wherein the following biomarkers are measured in combination;
 isocitric acid in the cerebrospinal fluid sample collected from a subject;
 cis-aconitic acid in the cerebrospinal fluid sample collected from a subject;
 serine in a serum sample collected from the subject;
 uric acid in a serum sample collected from the subject; and
 citric acid in a serum sample collected from the subject.

8. The method of any preceding or following embodiment/feature/aspect, wherein the following biomarkers are measured in combination;
 pyruvic acid in a serum sample collected from the subject;
 N-acetylglutamic acid in a serum sample collected from the subject;
 2-oxoglutaric acid in a serum sample collected from the subject;
 β-alanine in a serum sample collected from the subject;
 arginine in a serum sample collected from the subject; and
 serine in a serum sample collected from the subject.

9. The method of any preceding or following embodiment/feature/aspect, further comprising collecting cerebrospinal fluid from the subject, collecting serum from the subject, or both.

10. The method of any preceding or following embodiment/feature/aspect, wherein the collecting is performed when the subject is euthymic.

11. The method of any preceding or following embodiment/feature/aspect, wherein the subject has had at least one bipolar episode, at least one manic episode, at least one hypomanic episode, at least one depressive episode, or any combination thereof.

12. The method of any preceding or following embodiment/feature/aspect, further comprising performing a second diagnostic test for the bipolar disorder, wherein the second diagnostic test is not based on a biomarker.

13. The method of any preceding or following embodiment/feature/aspect, wherein the bipolar disorder is a bipolar I disorder, a bipolar II disorder, rapid-cycling bipolar disorder, bipolar disorder not otherwise specified, cyclothymia, or any combination thereof.

14. The method of any preceding or following embodiment/feature/aspect, further comprising administering at least one bipolar medication to the subject.

15. The method of any preceding or following embodiment/feature/aspect, wherein the at least one bipolar medication comprises lithium, valproic acid, carbamazepine, oxcarbazepine, lamotrigine, lurasidone, divalproex, or any salt thereof, or any combination thereof 16. The method of any preceding or following embodiment/feature/aspect, wherein the at least one bipolar medication is administered before the measuring and comparing, after the measuring and comparing, or both.

17. The present invention further relates to a method of identifying a compound for preventing and/or treating a bipolar disorder, comprising:
    contacting a eukaryotic cell with a test compound;
    measuring an expression level of an isocitric acid dehydrogenase 3 α-subunit gene, an isocitric acid dehydrogenase 3 β-subunit gene, or both in the cell;
    comparing the expression level with a control expression level of the gene in an untreated eukaryotic cell, wherein an increased expression level of the at least one gene compared to the control expression level is indicative that the test compound is a candidate for preventing and/or treating a bipolar disorder.

18. The method of any preceding or following embodiment/feature/aspect, wherein the treated and untreated eukaryotic cells are mammalian cells.

19. The method of any preceding or following embodiment/feature/aspect, wherein the treated and untreated eukaryotic cells are human cells.

20. The method of any preceding or following embodiment/feature/aspect, wherein the treated and untreated eukaryotic cells comprise neurons, glial cells, or both.

21. The method of any preceding or following embodiment/feature/aspect, wherein the treated and untreated eukaryotic cells are genetically engineered to reduce expression of the isocitric acid dehydrogenase 3 α-subunit gene, the isocitric acid dehydrogenase 3 β-subunit gene, or both.

22. The method of any preceding or following embodiment/feature/aspect, further comprising:
    determining that the test compound is a candidate for preventing and/or treating a bipolar disorder;
    administering the test compound to an animal;
    measuring an expression the level of the isocitric acid dehydrogenase 3 α-subunit gene, the isocitric acid dehydrogenase 3 β-subunit gene, or both in a prefrontal cortex of the animal; and
    comparing the expression level with a control expression level of the at least one gene in a prefrontal cortex of an untreated animal, wherein an increased level of the at least one gene compared to the control expression level is indicative that the test compound is a bipolar disorder therapeutic.

23. The method of any preceding or following embodiment/feature/aspect, further comprising:
    selecting a test compound that decreased expression level of the at least one gene compared to the control expression level; and
    identifying the test compound as a candidate for preventing and/or treating a bipolar disorder.

24. The method of any preceding or following embodiment/feature/aspect, further comprising administering the identified compound to a subject.

25. The method of any preceding or following embodiment/feature/aspect, wherein the subject has been diagnosed with a bipolar disorder or a predisposition for a bipolar disorder.

26. The method of any preceding or following embodiment/feature/aspect, further comprising:
    measuring the amount of at least one biomarker in a sample from the subject;
    comparing the amount of at least one biomarker in the sample with a control amount of the at least one marker, wherein an increase or decrease of the amount of the at least one biomarker is indicative that the bipolar disorder has been treated or prevented.

27. The present invention further relates to a method of identifying a compound for preventing and/or treating bipolar disorder, comprising;
    administering a test compound to an animal;
    measuring an expression level of an isocitric acid dehydrogenase 3 α-subunit gene, an isocitric acid dehydrogenase 3 α-subunit gene, or both in a prefrontal cortex of the animal, and
    comparing the expression level with a control expression level of the at least one gene in a prefrontal cortex of an untreated animal, wherein an increased level of the at least one gene compared to the control expression level is indicative that the test compound is a candidate for preventing and/or treating bipolar disorder.

28. The method of any preceding or following embodiment/feature/aspect, wherein the animal is genetically engineered to reduce expression of the isocitric acid dehydrogenase 3 α-subunit gene, the isocitric acid dehydrogenase 3β-subunit gene, or both.

29. The method of any preceding or following embodiment/feature/aspect, wherein the animal is a non-human animal.

30. The method of any preceding or following embodiment/feature/aspect, further comprising:
    selecting a test compound that decreased expression level of the at least one gene compared to the control expression level; and
    identifying the test compound as a candidate for preventing and/or treating a bipolar disorder.

31. The present invention further relates to a method of identifying a compound for preventing and/or treating bipolar disorder, comprising;
    contacting a eukaryotic cell with a test compound in a culture;
    measuring an amount of at least one of the following biomarkers in the culture, isocitric acid, cis-aconitic acid, pyruvic acid, N-acetylglutamic acid, 2-oxoglutaric acid, β-alanine, arginine, serine, uric acid, and citric acid; and
    comparing the amount of the at least one biomarker with a control amount of the at least one biomarker in a culture of untreated eukaryotic cells, wherein a decrease in the amount of isocitric acid, a decrease in the amount of cis-aconitic acid, a decrease in the amount of pyruvic acid, a decrease in the amount of N-acetylglutamic acid, a decrease in the amount of 2-oxoglutaric acid, an increase in the amount of β-alanine, an increase in the amount of arginine, an increase in the amount of serine, a decrease in the amount of uric acid, and an increase in the amount of citric acid, in comparison to the control amount of the at least one biomarker are indicative that the test compound is a candidate for preventing and/or treating bipolar disorder.

32. The method of any preceding or following embodiment/feature/aspect, wherein the at least one biomarker comprises isocitric acid, and the cell is genetically engineered to reduce expression of isocitric acid dehydrogenase 3 β-subunit gene, a isocitric acid dehydrogenase 3 β-subunit gene, or both.

33. The method of any preceding or following embodiment/feature/aspect, further comprising:
selecting a test compound that increased or decreased expression level of the at least one gene as specified compared to the control expression level;
identifying the test compound as a candidate for preventing and/or treating a bipolar disorder.

34. The present invention further relates to a method of identifying a compound for preventing and/or treating bipolar disorder, comprising:
administering a test compound to an animal;
measuring an amount of at least one of the following biomarkers,
isocitric acid in a cerebrospinal fluid sample collected from the animal,
cis-aconitic acid in a cerebrospinal fluid sample collected from the animal,
pyruvic acid in a serum sample collected from the animal,
N-acetylglutamic acid in a serum sample collected from the animal,
2-oxoglutaric acid in a serum sample collected from the animal,
β-alanine in a serum sample collected from the animal,
arginine in a serum sample collected from the animal,
serine in a serum sample collected from the animal,
uric acid in a serum sample collected from the animal, and
citric acid in a serum sample collected from the animal; and
comparing the amount of the at least one biomarker with a control amount of at least one biomarker in a corresponding sample collected from an untreated animal, wherein a decrease in the amount of isocitric acid, a decrease in the amount of cis-aconitic acid, a decrease in the amount of pyruvic acid, a decrease in the amount of N-acetylglutamic acid, a decrease in the amount of 2-oxoglutaric acid, an increase in the amount of β-alanine, an increase in the amount of arginine, an increase in the amount of serine, a decrease in the amount of uric acid, and an increase in the amount of citric acid, in comparison to the control amount of the at least one biomarker is indicative that the test compound is a candidate for preventing and/or treating bipolar disorder.

35. The method of any preceding or following embodiment/feature/aspect, wherein the at least one biomarker comprises isocitric acid, and the animal is genetically engineered to reduce expression of isocitric acid dehydrogenase 3 α-subunit gene, a isocitric acid dehydrogenase 3 β-subunit gene, or both.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of treating a bipolar disorder in a subject, the method comprising:
collecting, from the subject, a cerebrospinal fluid sample or both a cerebrospinal fluid sample and a serum sample, wherein the cerebrospinal fluid sample comprises at least one biomarker comprising isocitric acid, or at least two biomarkers comprising isocitric acid and cis-aconitic acid and wherein the serum sample comprises at least one biomarker selected from the group consisting of N-acetylglutamic acid, 2-oxoglutaric acid, and serine;
measuring an amount of the at least one biomarker in the cerebrospinal fluid sample or both of the cerebrospinal fluid sample and the serum sample collected from the subject;
comparing the amount of the at least one biomarker in the cerebrospinal fluid sample or both of the cerebrospinal fluid sample and the serum sample collected from the subject with a control amount of the at least one biomarker in a corresponding sample collected from a subject without the bipolar disorder, wherein an increase in the amount of isocitric acid, an increase in the amount of cis-aconitic acid, an increase in the amount of N-acetylglutamic acid, an increase in the amount of 2-oxoglutaric acid, and a decrease in the amount of serine, in comparison to the control amount of the at least one biomarker are indicative that the subject has the bipolar disorder or a predisposition for the bipolar disorder; and
administering at least one bipolar medication selected from the group consisting of lithium, valproic acid, carbamazepine, oxcarbazepine, lamotrigine, lurasidone, divalproex, and a salt of lurasidone to the subject.

2. The method of claim 1, wherein the serum sample is collected from the subject and the at least one biomarker further comprises serine.

3. The method of claim 1, wherein the cerebrospinal fluid sample and the serum sample are both collected from the subject and each sample comprises at least one of the biomarkers.

4. The method of claim 1, wherein the cerebrospinal fluid sample, or both the cerebrospinal fluid sample and the serum sample are collected from the subject, and wherein at least two of the biomarkers are measured in combination.

5. The method of claim 1, wherein both the cerebrospinal fluid sample and the serum sample are collected from the subject, and wherein five of the biomarkers are measured in combination.

6. The method of claim 1, wherein the collecting is performed when the subject is euthymic.

7. The method of claim 1, wherein the subject has had at least one bipolar episode, at least one manic episode, at least one hypomanic episode, at least one depressive episode, or any combination thereof.

8. The method of claim 1, further comprising performing a second diagnostic test for the bipolar disorder, wherein the second diagnostic test is not based on a biomarker.

9. The method of claim 1, wherein the bipolar disorder is a bipolar I disorder, a bipolar II disorder, rapid-cycling bipolar disorder, bipolar disorder not otherwise specified, cyclothymia, or any combination thereof.

10. The method of claim 1, wherein the administering of the at least one bipolar medication is carried out before the measuring and comparing, after the measuring and comparing, or both.

11. A method of treating a bipolar disorder in a subject, the method comprising:
    collecting, from the subject, a cerebrospinal fluid sample, a serum sample, or both a cerebrospinal fluid sample and a serum sample, wherein the cerebrospinal fluid sample comprises at least one biomarker selected from the group consisting of isocitric acid and cis-aconitic acid, and wherein the serum sample comprises at least one biomarker selected from the group consisting of N-acetylglutamic acid, 2-oxoglutaric acid, and serine;
    measuring an amount of the at least one biomarker in one or both of the cerebrospinal fluid sample and the serum sample collected from the subject;
    comparing the amount of the at least one biomarker in one or both of the cerebrospinal fluid sample and the serum sample collected from the subject with a control amount of the at least one biomarker in a corresponding sample collected from a subject without the bipolar disorder, wherein an increase in the amount of isocitric acid, an increase in the amount of cis-aconitic acid, an increase in the amount of N-acetylglutamic acid, an increase in the amount of 2-oxoglutaric acid, and a decrease in the amount of serine, in comparison to the control amount of the at least one biomarker are indicative that the subject has the bipolar disorder or a predisposition for the bipolar disorder; and
    administering at least one bipolar medication selected from the group consisting of lithium, valproic acid, carbamazepine, oxcarbazepine, lamotrigine, lurasidone, divalproex, and a salt of lurasidone to the subject, and
wherein:
    the at least one biomarker of the serum sample further comprises at least one further biomarker selected from the group consisting of pyruvic acid, β-alanine, arginine, uric acid, and citric acid, and
    wherein the method further comprises:
    measuring an amount of at least one further biomarker in the serum sample collected from the subject; and
    comparing the amount of the at least one further biomarker with a control amount of the at least one further biomarker in a corresponding sample collected from a subject without the bipolar disorder,
    wherein an increase in the amount of pyruvic acid, a decrease in the amount of β-alanine, a decrease in the amount of arginine, an increase in the amount of uric acid, and a decrease in the amount of citric acid, in comparison to the control amount of the at least one biomarker are indicative that the subject has the bipolar disorder or a predisposition for the bipolar disorder and wherein a) both the cerebrospinal fluid sample and the serum sample are collected from the subject, and wherein the following biomarkers are measured in combination:
    isocitric acid;
    cis-aconitic acid;
    serine;
    uric acid; and
    citric acid;
or b) wherein the serum sample is collected from the subject, and wherein the following biomarkers are measured in combination:
    pyruvic acid;
    N-acetylglutamic acid;
    2-oxoglutaric acid;
    β-alanine;
    arginine; and
    serine.

* * * * *